US012131801B2

(12) United States Patent
Gligorijevic et al.

(10) Patent No.: US 12,131,801 B2
(45) Date of Patent: Oct. 29, 2024

(54) FUNCTION GUIDED IN SILICO PROTEIN DESIGN

(71) Applicants: Genentech, Inc., South San Francisco, CA (US); Simons Foundation, New York, NY (US); New York University, New York, NY (US)

(72) Inventors: Vladimir Gligorijevic, New York, NY (US); Richard Bonneau, New York, NY (US); Kyunghyun Cho, New York, NY (US)

(*) Notice: Subject to any disclaimer, the term of this patent is extended or adjusted under 35 U.S.C. 154(b) by 0 days.

(21) Appl. No.: 18/513,348

(22) Filed: Nov. 17, 2023

(65) Prior Publication Data

US 2024/0087674 A1    Mar. 14, 2024

Related U.S. Application Data

(63) Continuation of application No. PCT/US2022/029457, filed on May 16, 2022.

(60) Provisional application No. 63/189,601, filed on May 17, 2021.

(51) Int. Cl.
*G01N 33/48* (2006.01)
*G16B 15/00* (2019.01)
*G16B 30/20* (2019.01)

(52) U.S. Cl.
CPC ............ *G16B 15/00* (2019.02); *G16B 30/20* (2019.02)

(58) Field of Classification Search
None
See application file for complete search history.

(56) References Cited

U.S. PATENT DOCUMENTS

2021/0193259 A1* 6/2021 Bikard .................. G16B 20/00

FOREIGN PATENT DOCUMENTS

| WO | WO 2019/097014 | 5/2019 |
| WO | WO 2020/208555 | 10/2020 |
| WO | WO 2020/236839 | 11/2020 |

OTHER PUBLICATIONS

Po-Ssu Huang, Scott E. Boyken, and David Baker. The coming of age of de novo protein design. Nature, 537(7620):320-327, 2016.
Philip A. Romero and Frances H. Arnold. Exploring protein fitness landscapes by directed evolution. Nature Reviews Molecular Cell Biology, 10(12):866-876, 2009.
Ethan C. Alley, Grigory Khimulya, Surojit Biswas, Mohammed AlQuraishi, and George M. Church. Unified rational protein engineering with sequence-based deep representation learning. Nature Methods, 16(12):1315-1322, 2019.
Tristan Bepler and Bonnie Berger. Learning protein sequence embeddings using information from structure. In International Conference on Learning Representations, 2019.
Alexander Rives, Joshua Meier, Tom Sercu, Siddharth Goyal, Zeming Lin, Demi Guo, Myle Ott, C. Lawrence Zitnick, Jerry Ma, and Rob Fergus. Biological structure and function emerge from scaling unsupervised learning to 250 million protein sequences. bioRxiv, 2020.
Ali Madani, Bryan McCann, Nikhil Naik, Nitish Shirish Keskar, Namrata Anand, Raphael R. Eguchi, Po-Ssu Huang, and Richard Socher. Progen: Language modeling for protein generation. bioRxiv, 2020.
Roshan Rao, Nicholas Bhattacharya, Neil Thomas, Yan Duan, Peter Chen, John Canny, Pieter Abbeel, and Yun Song. Evaluating protein transfer learning with tape. In H. Wallach, H. Larochelle, A. Beygelzimer, F. Alché-Buc, E. Fox, and R. Garnett, editors, Advances in Neural Information Processing Systems 32, pp. 9689-9701. Curran Associates, Inc., 2019.
Jung-Eun Shin, Adam J Riesselman, Aaron W Kollasch, Conor McMahon, Elana Simon, Chris Sander, Aashish Manglik, Andrew C Kruse, and Debora S Marks. Protein design and variant prediction using autoregressive generative models. Nature communications, 12(1):1-11,2021.
Amos Bairoch and Rolf Apweiler. The SWISS-PROT protein sequence database and its supplement TrEMBL in 2000. Nucleic Acids Research, 28(1):45-48, 01 2000.
Vladimir Gligorijevic, P. Douglas Renfrew, Tomasz Kosciolek, Julia Koehler Leman, Kyunghyun Cho, Tommi Vatanen, Daniel Berenberg, Bryn Taylor, Ian M. Fisk, Ramnik J. Xavier, Rob Knight, and Richard Bonneau. Structure-based function prediction using graph convolutional networks. bioRxiv, 2019.
Namrata Anand and Possu Huang. Generative modeling for protein structures. In S. Bengio, H. Wallach, H. Larochelle, K. Grauman, N. Cesa-Bianchi, and R. Garnett, editors, Advances in Neural Information Processing Systems 31, pp. 7494-7505. Curran Associates, Inc., 2018.
Raphael R. Eguchi, Namrata Anand, Christian A. Choe, and Po-Ssu Huang. Ig-vae: Generative modeling of immunoglobulin proteins by direct 3d coordinate generation. bioRxiv, 2020.
Sivaraman Balakrishnan, Hetunandan Kamisetty, Jaime G. Carbonell, Su-In Lee, and Christopher James Langmead. Learning generative models for protein fold families. Proteins: Structure, Function, and Bioinformatics, 79(4):1061-1078, 2011.

(Continued)

*Primary Examiner* — Anna Skibinsky
(74) *Attorney, Agent, or Firm* — Jones Day

(57) ABSTRACT

A protein design system includes one or more processors configured to modify, by a modifier, an input sequence corresponding to a protein, the input sequence comprising a data structure indicating a plurality of amino acid residues of the protein; map, by an encoder, the modified sequence to a latent space; predict, by a length predictor, a length difference between the mapped sequence and a target sequence based on at least one target function of the target sequence; identify, by a function classifier, at least one sequence function of the modified sequence; transform, by a length transformer, the modified sequence based on the length difference and the at least one sequence function; and generate, by a decoder, a candidate for the target sequence based on the transformed sequence.

21 Claims, 20 Drawing Sheets

(56) References Cited

OTHER PUBLICATIONS

Alex Hawkins-Hooker, Florence Depardieu, Sebastien Baur, Guillaume Couairon, Arthur Chen, and David Bikard. Generating functional protein variants with variational autoencoders. BioRxiv, 2020.

Kristian Davidsen, Branden J Olson, III DeWitt, William S, Jean Feng, Elias Harkins, Philip Bradley, and IV Matsen, Frederick A. Deep generative models for t cell receptor protein sequences. eLife, 8:e46935, 2019.

Joe G. Greener, Lewis Moffat, and David T. Jones. Design of metalloproteins and novel protein folds using variational autoencoders. Scientific Reports, 8(1):16189, 2018.

Pascal Vincent, Hugo Larochelle, Yoshua Bengio, and Pierre-Antoine Manzagol. Extracting and composing robust features with denoising autoencoders. In Proceedings of the Twenty-fifth International Conference on Machine Learning (ICML'08), pp. 1096-1103. ACM, 2008.

Pascal Vincent, Hugo Larochelle, Isabelle Lajoie, Yoshua Bengio, Pierre-Antoine Manzagol, and Léon Bottou. Stacked denoising autoencoders: Learning useful representations in a deep network with a local denoising criterion. Journal of machine learning research, 11(12), 2010.

Pascal Vincent. A connection between score matching and denoising autoencoders. Neural computation, 23(7):1661-1674, 2011.

Yoshua Bengio, Li Yao, Guillaume Alain, and Pascal Vincent. Generalized denoising auto-encoders as generative models. In Proceedings of the 26th International Conference on Neural Information Processing Systems—vol. 1, NIPS'13, p. 899-907, Red Hook, NY, USA, 2013. Curran Associates Inc.

Kyunghyun Cho. Noisy parallel approximate decoding for conditional recurrent language model, 2016.

Jason Lee, Elman Mansimov, and Kyunghyun Cho. Deterministic non-autoregressive neural sequence modeling by iterative refinement. In Proceedings of the 2018 Conference on Empirical Methods in Natural Language Processing, 2018.

Jiatao Gu, James Bradbury, Caiming Xiong, Victor O.K. Li, and Richard Socher. Non-autoregressive neural machine translation. In International Conference on Learning Representations, 2018.

Raphael Shu, Jason Lee, Hideki Nakayama, and Kyunghyun Cho. Latent-variable non-autoregressive neural machine translation with deterministic inference using a delta posterior. AAAI, 2020.

Jason Lee, Dustin Tran, Orhan Firat, and Kyunghyun Cho. On the discrepancy between density estimation and sequence generation. arXiv preprint arXiv:2002.07233, 2020.

Samy Bengio, Oriol Vinyals, Navdeep Jaitly, and Noam Shazeer. Scheduled sampling for sequence prediction with recurrent neural networks. In Proceedings of the 28th International Conference on Neural Information Processing Systems—vol. 1, NIPS'15, p. 1171-1179, Cambridge, MA, USA, 2015. MIT Press.

Marc'Aurelio Ranzato, Sumit Chopra, Michael Auli, and Wojciech Zaremba. Sequence level training with recurrent neural networks, 2016.

Felix Hill, Kyunghyun Cho, and Anna Korhonen. Learning distributed representations of sentences from unlabelled data. CoRR, abs/1602.03483, 2016.

Jianyi Yang, Ivan Anishchenko, Hahnbeom Park, Zhenling Peng, Sergey Ovchinnikov, and David Baker. Improved protein structure prediction using predicted interresidue orientations. Proceedings of the National Academy of Sciences, 117(3):1496-1503, 2020.

Gifford et al. Structures and metal-ion-binding properties of the $Ca2+$-binding helix-loop-helix EF-hand motifs. Biochemical Journal, 405(2):199-221, 06 2007.

Dudev et al., Competition among metal ions for protein binding sites: Determinants of metal ion selectivity in proteins. Chemical Reviews, 114(1):538-556, Jan. 2014.

Apweiler et al., Uniprot: the universal protein knowledgebase. Nucleic Acids Res, 32:115-119, 2004.

Vaswani et al., 2017, "Attention is all you need," In Proceedings of the 31st International Conference on Neural Information Processing Systems, NIPS'17, p. 6000-6010, Curran Associates Inc.

International Search Report and Written Opinion dated Aug. 22, 2022 for International Patent Application PCT/US2022/029457 (13 pages).

* cited by examiner

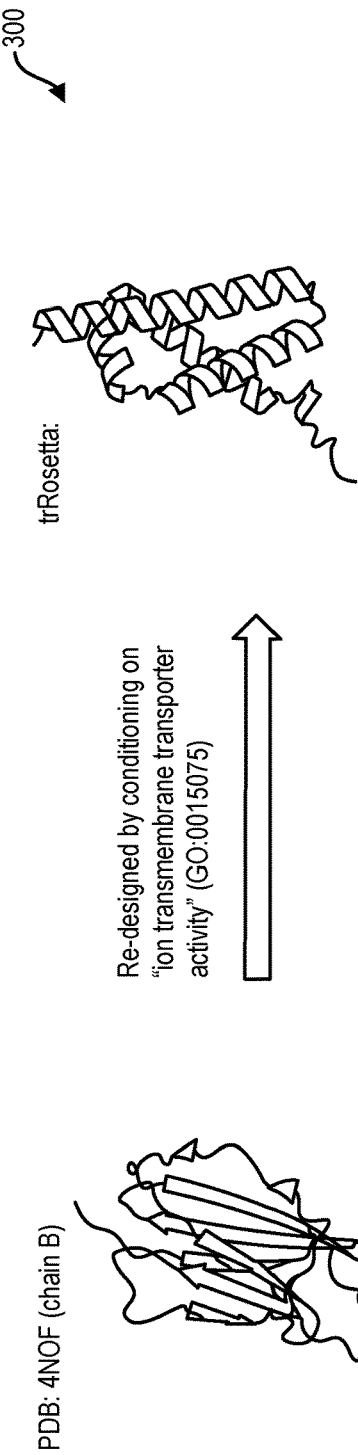

Input sequence:
>>IQRTPKIQVYSRHPAENGKSNFLNCYVSGFHPSDIEVDLLKNGERIEKV
EHSDLSFSKDWSFYLLYTEFTPTEKDEYACRVNHVTLSQPKIVKWDRDM Known functions:
protein binding
identical protein binding
protein homodimerization activity
protein dimerization activity PDB: 4NOF (chain B)

Re-designed by conditioning on "ion transmembrane transporter activity" (GO:0015075)

trRosetta:

Designed sequence:
>>IRPPQQVRHYPENNKKMMHFYAELLKYLKKGEEKVVAKRASFP
QLAAYYSWLLEEAVTTQQKKFDDAALYYALLTTVYLPAAFLVDDM Predicted functions:

| GO term | Name | Prob | Reliability |
|---|---|---|---|
| GO:0055085 | transmembrane transport | 0.962 | H |
| GO:0034220 | ion transmembrane transport | 0.942 | H |
| GO:0051171 | regulation of nitrogen compound metabolic process | 0.926 | H |
| GO:0006811 | ion transport | 0.916 | H |
| GO:0019222 | regulation of metabolic process | 0.915 | H |
| GO:1903506 | regulation of nucleic acid-templated transcription | 0.911 | H |
| GO:0006810 | transport | 0.910 | H |
| GO:0051252 | regulation of RNA metabolic process | 0.909 | H |

PDB 1AGY (chain A)

>LGRTTRDDLINGNSASCRDVIFIYARGSTETGNLGTLGPSIASNLESA
FGKDGVWIQGVGGAYRATLGDNALPRGTSSAAIREMLGLFQQANTKC
PDATLIAGGYSQGAALAAASIEDLDSAIRDKIAGTVLFGYTKNLQNRGR
IPNYPADRTKVFCNTGDLVCTGSLIVAAPHLAYGPDARGPAPEFLIEKV
RAVRGSA

500

Designed (sample 55)

>HLGLTCRDDLICIGGNSAICPDLIFIYSRGSCETGNDGTLLPIIASN
SMFHKDGVIIAGSGGALRATLGMAALPRGTYSSAAVGELLGLAQP
ANTPRDATIIAGGYSQGAALKAPFSIDADDSAIRDDAAGIVLLGVT
EILNGYGGIPLNYPADVTKLACNNGDLVNTGAIIVAAPHLLAGPPAR
GPPEETLIETFRAVRISA

Aligned: 500

500

```
1AGY_A        -LGRTTRDDL--INGNSASCRDVIFIYARGN T  ETGNLGTLGPSIASSLESAFGKDGVMIQ
sample_55     HLGLTCRDDLICIGGNSAICPDLIFIYSRGS C  ETGNDGTLLPIIAS-SNSMFHKDGVIIA
sample_107    HLGLTTRDDLICIGGLSAICPDGIFISARGP S  ETGNDGTLGPIIAS-SNSAFHKDGVIIQ
sample_435    HLGLTGRDDLICIGGNSAICPDLIFIYARGP S  ETGNDGTLGPIIAD-SNSAFHKLGVIIQ
sample_538    HLGLTTRDDLICIGGNSAICPDLIFIYYRGP S  ETTNNETVGPIIAS-SESAFHKDGFNII
sample_645    HLGLTTRDDLICEGGNSAICPDLIFIYARGS E  SNGNDGTLGPIIAS-SNSAFHKDGVIIG
sample_693    HLGLTTRDDLICIGGNSAICPGLIFIYARGP S  ETGNDGTLGPIIAS-SNSAFHKDGVIIQ
sample_769    HLGLTTRDDLICIGGNSAICADLIFIYARGP S  ETGNDGTLGPIIAS-SNSFFHKDGVIHQ
sample_905    HLGLTTRDDLICIGGNSAICPDLIFIYARGP S  ETGNDGTLGGIIAS-SGSAFHKDGVEIQ
sample_1100   HLGLTTIDDLICIGGCSAICPDLIFIYARGP S  ETGNDGTLGPIIAS-SNSAFHKDGVIIQ
sample_1551   HL-LFTNDD-LIIGGISAICPDAIFFYPRGS S  EEVNLGELGPIXAG-MNSSFGKDGVSSQ
sample_1850   HLELTTRDDLICIGGNSAICIKLIFIKARGS S  ETGNDGTLGPIIAS-SNSAFHNDGVTIQ
sample_2660   HLGLTTNDDLICIGGNSAICPDLIFIYARGP S  ETGNDGTLGPIIAS-SNSAFHKDGVIIQ
sample_2890   HKGLTTNDDLIVIGGNSAGCPDLIFIYARGS S  ETGDDGTLGPIIAS-HNSAFKEDGVIIQ 1AGY_A        GVGGATRATLGDHALPR-GT-SSAAIREMLGLFQQANTKCPDATLIAGGYB QC AAL--AA
sample_55     GSGGALRATLGMAALPR-GTYSSAAVGELLGLAQPANTPE-DATIIAGGYB SQ GAALKAP
sample_107    GSGGALRATLGMQALPR-GTYSSAAIGELLGLAMPAKTKD-DATIIAGGYB QQ GAALKAP
sample_435    GSGGALRAYLGMQALPR-GTYSSAAIGELLGLAQPANTKD-DATIIAGGYB QQ GAALKAP
sample_538    GSSGGLRATLLMMAAPMRGTYSAAIGGLLGGLQQPANTRC-DATIIAGGYB QG ALLKKPF
sample_645    GSGGALRATLGMQAGLL-GTYSSAAIGELLGLAQPANTRF-DATIIAGGYB SN GAALKAP
sample_693    GSGGALRATLMMQALPR-GTYSSAAIGELLGLAQPANTRR-DAVIIMGGYB QQ GAALKAP
sample_769    GSGGALRATLGMQALPK-GTYISAAIGELLGLAQPANTKK-DAEIIAGGYB QQ GAALKAP
sample_905    GRGGALRATGGMQALPR-GTYSSAAIGELLGLAQPANTKE-DATIIAGGYB QQ GAALKAP
sample_1100   GSGGALRATLGMQALPR-GTHSSAAIGELLGLAQPANTWD-DATIIAGGYB QQ GAALKAP
sample_1551   GVCDALRATGGMHALPA-GTAE-AAIHELL-WLQPANKKI-DATLIAGGYB DQ GAALLAP
sample_1850   GSWGALRTTLGKQLLPI-GTYSSGAIGELLGLAQPANTPD-DATIIAGGYB SQ GAALKAP
sample_2660   GSDGALRGTLGMQALPR-GTYSSAAIGELLGLAQPANTQE-DATIIAGGYB QQ GAALKAP
sample_2890   GSQGALRATLGGQALPR-GTYSSAAIGELLGLAQPANTKR-DATIIAGYYB SQ GAALKAP
```

```
1AGY_A        ASIEDLDSAIRDKIAGTVLFGYTKHLQNRGRIP-NYPADRTKVFCNTG D LVCTCSLIVAA
sample_55     FSIDADDSAIRDDAAGIVLLGVTEILNGYGGIPLNYPADVTKLACNNG D LVNTGAIIVAA
sample_107    FSIDALDSAIRDDAAGIVLLGVTELLNGYGGIPLNYPADVTKLACNNG D LVNTGAIIVAA
sample_435    FSINALDSAIRDDAAGIVLLGVTEILNGYGGIPLNYPADVTKLACNNG D LVNTGAIIVAA
sample_538    SIDDADDSIIRDDACGIVLLGTTELLNGYGIHPLYYADDTTLLACNGD D LVLTGAIIVAA
sample_645    FSIDALDSAIRDDAAGIVLLGVTEILNGYGGIPLNRPVDVTKLACNNG D LVNTSAIIVAA
sample_693    FSIDALDSAVRDDAAGIVLLGVTELLNGYGGIPLNYPADVTKLACNNG D LVNTGAIIVAA
sample_769    ISIDALDSAIRDDAAGIVLLGVTEILNGYKTPILNYPADDTKLACNNG D LVNTGAIIVAA
sample_905    ISIDALDSAIRDDAAGIVLLGVTEILNGYGGIPLCYPDDVTKLACNNG D LLNTGAIIVAA
sample_1100   FSIDALDSAIRDDAAGIVLLGGTEILNGYGGIPLNYPADVTKLACNNG D LVNTGAIIVAA
sample_1551   FSIDALDSAIYDDAAGIVLLGVTRI-TGYGGIPLVYPADVTKVCCNTG D LVCTRAIIVAI
sample_1850   FSIDAADSAARDDAAGIVLLGVTEILNGYGGIPLNYPADVTKLACNIG D LVNTGAIIVAA
sample_2660   FSIGALDSAIRDDAAGIVLLGVTWILNGYGGIPLNYPADVTKLLCNNG D LVNGGAPIVAA
sample_2890   FSITALDARTRDDAAGIILLGVTEILNGYGGILLNYPADVTKLACNNG D AVITGAIIVAA 1AGY_A        F N LAYGPDAKGPAPEFLIEKVRAVKGSA
sample_55     F N LLAGPPAKGPPEETLIETFRAVKISA
sample_107    F N LLYGPPARGPPEETLIETFRAVRISA
sample_435    F N LLYGPPARRGPEETLIETFRPVKISA
sample_538    F N LLYNAPARGPPEETLIETFRAVKISA
sample_645    F M LLYGPFARGPPEETLIETFRAVKISA
sample_693    F N LLYGPPARGPPEELLIETFRAVKISA
sample_769    F N LLYIPPARGPPEETLIETFRAVKISA
sample_905    F N LLYIPPARGPPEETLIETFRAVFILA
sample_1100   F N LLYGPPARKPPEETLIFTPRAVKISA
sample_1551   F N LAYGQPARGPIPEYLIETPRAVKISA
sample_1850   F N LQYGGPARGPPEETLIETFRAVRISA
sample_2660   F N LLYGPPARGPPEEQLIETFRAVRISA
sample_2890   F N LLYGPPNRGPPEETLIETFRVVRIIA
```

FIG. 5E Cont.

FUNCTION GUIDED IN SILICO PROTEIN DESIGN

CROSS-REFERENCE TO RELATED APPLICATIONS

This application is a bypass continuation of International Application No. PCT/US2022/029457, filed May 16, 2022, which claims priority to U.S. Provisional Application No. 63/189,601, entitled "SYSTEM AND METHODS FOR IN-SILICO FUNCTION GUIDED PROTEIN DESIGN" and filed on May 17, 2021, the disclosure of each of which is incorporated herein by reference in its entirety.

TECHNICAL FIELD

The subject matter described herein relates generally to protein design and more specifically to techniques for designing protein sequences having certain desired functions.

INTRODUCTION

Proteins are responsible for many essential cellular functions including, for example, enzymatic reactions, transport of molecules, regulation and execution of a number of biological pathways, cell growth, proliferation, nutrient uptake, morphology, motility, intercellular communication, and/or the like. A protein structure may include one or more polypeptides, which are chains of amino acid residues linked together by peptide bonds. The sequence of amino acid residues in the polypeptide chains forming the protein structure determines the protein's three-dimensional structure (e.g., the protein's tertiary structure). Moreover, the sequence of amino acids in the polypeptide chains forming the protein determines the protein's underlying functions. As such, the primary objective of de novo protein design includes constructing one or more sequences of amino acid residues that exhibit certain traits. For example, in the case of large molecule drug discovery, de novo protein design will often seek to identify sequences of amino acid residues (e.g., antibodies and/or the like) capable of binding to an antigen such as a viral antigen, a tumor antigen, and/or the like.

SUMMARY

Systems, methods, and articles of manufacture, including computer program products, are provided for in silico protein design. In some example embodiments, there is provided a system that includes at least one processor and at least one memory. The at least one memory may include program code that provides operations when executed by the at least one processor. The operations may include: identifying a protein structure having a first sequence of residues; generating, using a protein design computational model, a second sequence of residues comprising at least one corruption relative to the first sequence of residues; and generating, using the protein design computational model, a modified protein structure having the second sequence of residues.

In some variations, one or more features disclosed herein including the following features can optionally be included in any feasible combination. The protein design computational model may include a machine learning model trained to generate the second sequence of residues.

In some variations, the machine learning model may generate the second sequence of residues by at least sampling a data distribution learned through training.

In some variations, the data distribution may correspond to a reduced dimension representation of data corresponding to a plurality of known protein sequences. At least a portion of the plurality of sequence of residues may be associated with one or more known functions.

In some variations, the sampling of the data distribution may include generating a corrupted sequence by modifying the first sequence of residues, encoding the corrupted sequence to generate an encoding having a length corresponding to a quantity of residues present in the encoding, generating an intermediate sequence by altering the length of the encoding of the corrupted sequence, and generating, based at least on a decoding of the intermediate sequence, the second sequence of residues.

In some variations, the decoding of the intermediate sequence may include determining, for each position within the intermediate sequence, a probability distribution across a vocabulary of possible amino acid residues.

In some variations, the probability distribution may be determined by applying one or more of autoregressive modeling, non-autoregressive modeling, and condition random fields.

In some variations, the sampling of the data distribution may further include applying, to the encoding of the corrupted sequence, a function classifier to identify one or more functions associated with a corresponding protein structure.

In some variations, the sampling of the data distribution may further include generating another encoding of a different corrupted sequence in response to the function classifier determining that the corresponding protein structure lacks a desired function and/or exhibits an undesired function.

In some variations, the sampling of the data distribution may be performed for a threshold quantity of iterations.

In some variations, the sampling of the data distribution may be performed until a threshold quantity of protein structures are identified.

In some variations, the sampling of the data distribution may be performed until a threshold quantity of protein structures exhibiting a desired function and/or lacking an undesired function are identified.

In some variations, the at least one corruption may include inserting a residue into the first sequence of residues, deleting a residue from the first sequence of residues, and modifying a residue present in the first sequence of residues.

In some variations, the protein design computational model may include an autoencoder.

In some variations, the protein design computational model may include a denoising autoencoder (DAE).

In some variations, the protein design computational model may includes a length predictor configured to determine, based at least on an embedding of the second sequence of residues, a length change between the first sequence of residues and the second sequence of residues.

In some variations, the length predictor may determine the length change by applying, to a plurality of vectors comprising the embedding of the second sequence of residues, a pooling operation to generate a single vector representation of the encoding of the second sequence of residues.

In some variations, the length predictor may further determine the length change by applying, to the single vector representation of the embedding of the second sequence of residues, a neural network configured to determine a categorical distribution of possible length changes between the first sequence of residues and the second sequence of residues.

In some variations, the pooling operation may be a mean pooling operation.

In some variations, the length predictor may include an encoder stack of a transformer deep learning model. The encoder stack may generate a first plurality of vectors representative of a second plurality of vectors comprising the embedding of the second sequence of residues.

In some variations, the length predictor may further include a neural network configured to determine a categorical distribution of possible length changes between the first sequence of residues and the second sequence of residues.

In some variations, the encoder stack may include an attention mechanism that generates, as a part of the first plurality of vectors, a vector including information from other vectors in the first plurality of vectors. The neural network may determine the categorical distribution of possible length changes based on the vector.

In some variations, the neural network may determine, for each vector included in the first plurality of vectors, an individual categorical distribution of possible length changes. The categorical distribution of possible length changes may be determined based on the individual categorical distribution of possible length changes determined for each vector included in the first plurality of vectors.

In some variations, the categorical distribution of possible length changes may correspond to an average of the individual categorical distribution of possible length changes determined for each vector included in the first plurality of vectors.

In some variations, the protein design computational model may includes a length transformer configured to generate, based at least on the length change, a length transformed embedding of the second sequence of residues. The protein design computational model may generate the second sequence of residues by at least decoding the length transformed embedding of the second sequence of residues.

In some variations, the length transformed embedding may include a first quantity of vectors and the embedding of the second sequence of residues may include a second quantity of vectors. A difference between the first quantity of vectors and the second quantity of vectors may correspond to the length change.

In some variations, the length transformer may include a transformer deep learning model.

In some variations, the transformer deep learning model may generate the length transformed embedding by applying, based at least on a first length change to one or more preceding portions of the embedding of the second sequence of residues, a second length change to one or more subsequent portions of the embedding of the second sequence of residues.

In some variations, the transformer deep learning model may include an encoder and a decoder. The decoder may generate the length transformed embedding of the second sequence of residues by at least decoding an embedding of the first sequence of residues having at least one corruption and an output of the encoder operating on the embedding of the first sequence of residues.

In some variations, the length transformer may generate the length transformed embedding of the second sequence of residues by at least applying $z_t = \Sigma_{t'=1}^{|\tilde{L}|} \omega_{t,t'} h_{t'}$, and wherein z denotes the length transformed embedding of the second sequence of residues, h denotes a hidden vector set, and $$\omega_{t,t'}^t \propto \exp\left(-\beta \left| \frac{t}{|\tilde{x}| + \Delta l} - \frac{t'}{|\tilde{x}|} \right|\right).$$

In another aspect, there is provided a method for in silico protein design. The method may include: identifying a protein structure having a first sequence of residues; generating, using a protein design computational model, a second sequence of residues comprising at least one corruption relative to the first sequence of residues; and generating, using the protein design computational model, a modified protein structure having the second sequence of residues.

In some variations, one or more features disclosed herein including the following features can optionally be included in any feasible combination. The protein design computational model may include a machine learning model trained to generate the second sequence of residues.

In some variations, the machine learning model may generate the second sequence of residues by at least sampling a data distribution learned through training.

In some variations, the data distribution may correspond to a reduced dimension representation of data corresponding to a plurality of known protein sequences. At least a portion of the plurality of sequence of residues may be associated with one or more known functions.

In some variations, the sampling of the data distribution may include generating a corrupted sequence by modifying the first sequence of residues, encoding the corrupted sequence to generate an encoding having a length corresponding to a quantity of residues present in the encoding, generating an intermediate sequence by altering the length of the encoding of the corrupted sequence, and generating, based at least on a decoding of the intermediate sequence, the second sequence of residues.

In some variations, the decoding of the intermediate sequence may include determining, for each position within the intermediate sequence, a probability distribution across a vocabulary of possible amino acid residues.

In some variations, the probability distribution may be determined by applying one or more of autoregressive modeling, non-autoregressive modeling, and condition random fields.

In some variations, the sampling of the data distribution may further include applying, to the encoding of the corrupted sequence, a function classifier to identify one or more functions associated with a corresponding protein structure.

In some variations, the sampling of the data distribution may further include generating another encoding of a different corrupted sequence in response to the function classifier determining that the corresponding protein structure lacks a desired function and/or exhibits an undesired function.

In some variations, the sampling of the data distribution may be performed for a threshold quantity of iterations.

In some variations, the sampling of the data distribution may be performed until a threshold quantity of protein structures are identified.

In some variations, the sampling of the data distribution may be performed until a threshold quantity of protein structures exhibiting a desired function and/or lacking an undesired function are identified.

In some variations, the at least one corruption may include inserting a residue into the first sequence of residues, deleting a residue from the first sequence of residues, and modifying a residue present in the first sequence of residues.

In some variations, the protein design computational model may include an autoencoder.

In some variations, the protein design computational model may include a denoising autoencoder (DAE).

In some variations, the protein design computational model may includes a length predictor configured to determine, based at least on an embedding of the second sequence of residues, a length change between the first sequence of residues and the second sequence of residues.

In some variations, the length predictor may determine the length change by applying, to a plurality of vectors comprising the embedding of the second sequence of residues, a pooling operation to generate a single vector representation of the encoding of the second sequence of residues.

In some variations, the length predictor may further determine the length change by applying, to the single vector representation of the embedding of the second sequence of residues, a neural network configured to determine a categorical distribution of possible length changes between the first sequence of residues and the second sequence of residues.

In some variations, the pooling operation may be a mean pooling operation.

In some variations, the length predictor may include an encoder stack of a transformer deep learning model. The encoder stack may generate a first plurality of vectors representative of a second plurality of vectors comprising the embedding of the second sequence of residues.

In some variations, the length predictor may further include a neural network configured to determine a categorical distribution of possible length changes between the first sequence of residues and the second sequence of residues.

In some variations, the encoder stack may include an attention mechanism that generates, as a part of the first plurality of vectors, a vector including information from other vectors in the first plurality of vectors. The neural network may determine the categorical distribution of possible length changes based on the vector.

In some variations, the neural network may determine, for each vector included in the first plurality of vectors, an individual categorical distribution of possible length changes. The categorical distribution of possible length changes may be determined based on the individual categorical distribution of possible length changes determined for each vector included in the first plurality of vectors.

In some variations, the categorical distribution of possible length changes may correspond to an average of the individual categorical distribution of possible length changes determined for each vector included in the first plurality of vectors.

In some variations, the protein design computational model may includes a length transformer configured to generate, based at least on the length change, a length transformed embedding of the second sequence of residues. The protein design computational model may generate the second sequence of residues by at least decoding the length transformed embedding of the second sequence of residues.

In some variations, the length transformed embedding may include a first quantity of vectors and the embedding of the second sequence of residues may include a second quantity of vectors. A difference between the first quantity of vectors and the second quantity of vectors may correspond to the length change.

In some variations, the length transformer may include a transformer deep learning model.

In some variations, the transformer deep learning model may generate the length transformed embedding by applying, based at least on a first length change to one or more preceding portions of the embedding of the second sequence of residues, a second length change to one or more subsequent portions of the embedding of the second sequence of residues.

In some variations, the transformer deep learning model may include an encoder and a decoder. The decoder may generate the length transformed embedding of the second sequence of residues by at least decoding an embedding of the first sequence of residues having at least one corruption and an output of the encoder operating on the embedding of the first sequence of residues.

In some variations, the length transformer may generate the length transformed embedding of the second sequence of residues by at least applying $z_t = \Sigma_{t'=1}^{|\tilde{L}|} \omega_{t,t'} h_{t'}$, and wherein z denotes the length transformed embedding of the second sequence of residues, h denotes a hidden vector set, and $$\omega_{t,t'}^t \propto \exp\left(-\beta \left|\frac{t}{|\tilde{x}| + \Delta l} - \frac{t'}{|\tilde{x}|}\right|\right).$$

In another aspect, there is provided a computer program product including a non-transitory computer readable medium storing instructions. The instructions may cause operations may executed by at least one data processor. The operations may include: identifying a protein structure having a first sequence of residues; generating, using a protein design computational model, a second sequence of residues comprising at least one corruption relative to the first sequence of residues; and generating, using the protein design computational model, a modified protein structure having the second sequence of residues.

In another aspect, there is provided a method for training a protein sequence generator. The method can include retrieving, by one or more processors, a plurality of protein data structures, each protein data structure including a plurality of residues defining a polypeptide chain having a sequence length; modifying, by the one or more processors, each protein data structure of the plurality of protein data structures to generate a plurality of modified protein data structures; providing, by the one or more processors, the plurality of modified protein data structures as an input to a machine learning model for generating proteins; generating, by the machine learning model, a candidate output responsive to the input; and modifying, by the one or more processors, the machine learning model to satisfy a convergence condition based on the candidate output and the plurality of protein data structures.

In another aspect, there is provided a protein design system. The protein design system can include one or more processors configured to retrieve a plurality of protein data structures, each protein data structure comprising a plurality of residues defining a polypeptide chain having a sequence length; modify each protein data structure of the plurality of protein data structures to generate a plurality of modified protein data structures; provide the plurality of modified protein data structures as an input to a machine learning model for generating proteins; generate a candidate output responsive to the input; and modify the machine learning model (e.g., modify various parameters, such as weights or biases, of one or more layers of the machine learning model or a network used to implement the machine learning model), to satisfy a convergence condition based on the candidate output and the plurality of protein data structures.

In another aspect, there is provided a method for generating protein sequences. The method can include providing, by one or more processors as input to a machine learning model, at least one input protein data structure, the machine learning model trained to generate modified protein data structures based on training data comprising protein data structures and function assignments; and causing, by the one or more processors, the machine learning model to generate at least one modified protein data structure responsive to receiving the input.

In another aspect, there is provided a protein design system. The protein design system can include one or more processors configured to provide, as input to a machine learning model, at least one input protein data structure, the machine learning model trained to generate modified protein data structures based on training data comprising protein data structures and function assignments; and cause the machine learning model to generate at least one modified protein data structure responsive to receiving the input.

In another aspect, there is provided a protein design system. The protein design system can include one or more processors configured to modify, by a modifier, an input sequence corresponding to a protein, the input sequence comprising a data structure indicating a plurality of amino acid residues of the protein; map, by an encoder, the modified sequence to a latent space; predict, by a length predictor, a length difference between the mapped sequence and a target sequence based on at least one target function of the target sequence; identify, by a function classifier, at least one sequence function of the modified sequence; transform, by a length transformer, the modified sequence based on the length difference and the at least one sequence function; and generate, by a decoder, a candidate for the target sequence based on the transformed sequence.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to function guided in silico protein design, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 3 depicts a schematic diagram illustrating an example of a protein sequence redesigned by conditioning on an ion transmembrane transporter activity function, in accordance with some example embodiments;

When practical, similar reference numbers denote similar structures, features, or elements.

DETAILED DESCRIPTION

Figure 1A:
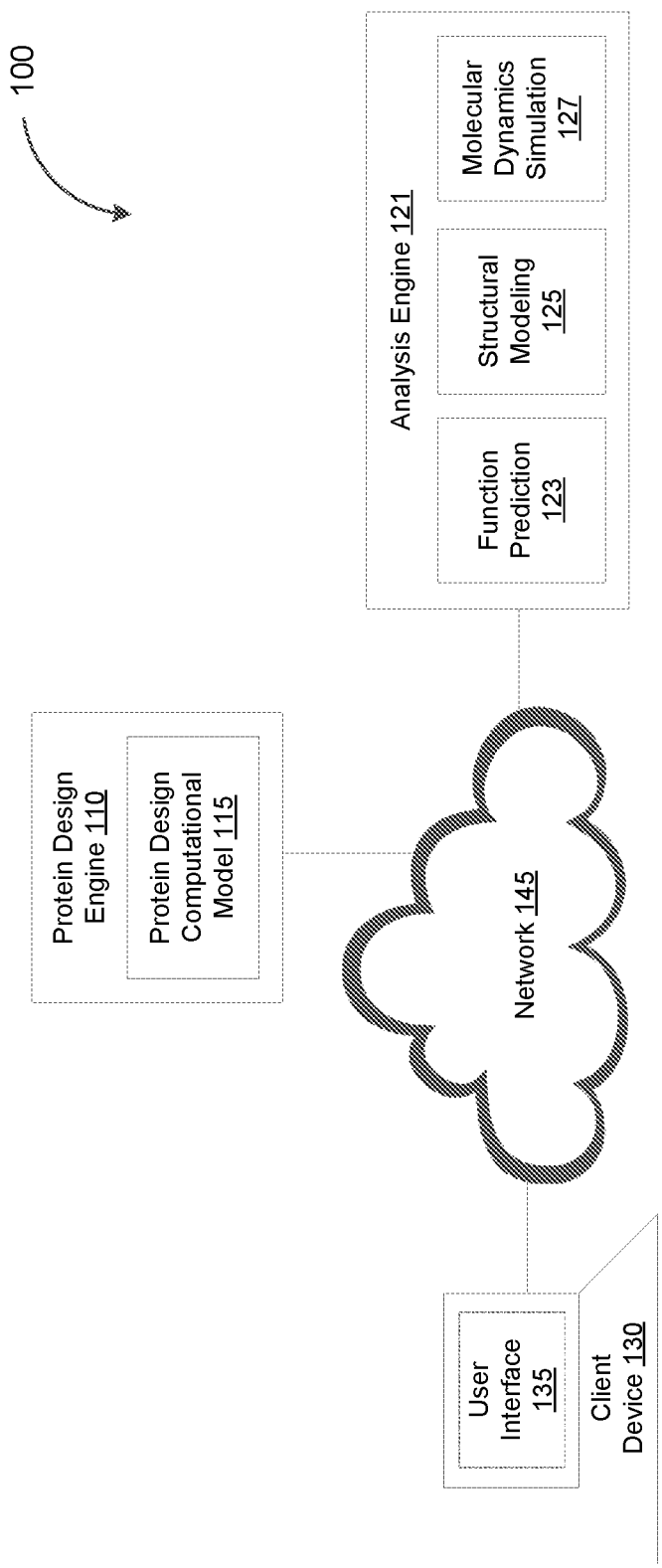
FIG. 1A depicts a system diagram illustrating an example of a protein design system, in accordance with some example embodiments.

De novo protein design aims to identify protein sequences (e.g., sequences of amino acid residues) that exhibit certain functionalities, such as binding affinity towards another molecule (e.g., a viral antigen, a tumor antigen, and/or the like). In doing so, de novo protein design has led to remarkable results in synthetic biology, agriculture, medicine, and nanotechnology, including the development of new enzymes, peptides, and biosensors. Nevertheless, de novo protein design is a challenging and resource intensive task at least because the combinatorial search space of every possible permutation of amino acid residues that can form a protein structure is vast but sparsely populated by sequences of amino acid residues that correspond to actually functional proteins. For example, the protein design space arising from all possible combinations of the 20 naturally occurring amino acids, for any protein of a given length, is a large combinatorial space that is only sparsely functional (the sparse mapping of protein sequence to protein folding is often referred to as the protein fitness landscape) with only a small fraction of sequences capable of folding into stable structural configurations to carry out specific functions.

In fact, the vast majority of protein sequences found in the protein sequence-function space will not exhibit any function at all, let alone a desired function such as a binding affinity towards certain molecules. This protein sequence-function space becomes even more immense when considering candidate protein sequences having variable lengths (e.g., candidate protein sequences with different quantities of amino acid residues). Thus, a brute force approach that indiscriminately examines every possible sequence of amino acid residues to identify sequences that exhibit a desired function, even when performed in silico, is too computationally expensive to be a feasible strategy for de novo protein design.

In view of the these challenges, conventional protein design techniques often start with a starting structure, which is predefined sequence or three dimensional scaffold that have been specifically identified as exhibiting characteristics likely to be successful for performing a particular function, and then progressively modifies this starting structure. For example, the starting structure may be predicted to fold into a pre-specified target structure capable of performing a desired function, such as by using the RosettaDesign protocol to generate an amino acid sequence that minimizes the energy of the folded state with a pre-defined backbone configuration derived from native or experimentally identified structures. Directed evolution is another example of a conventional protein design technique in which a sequence with a target function undergo successive iterations of diversification (e.g., introducing random mutations and creating more potential candidates), selection and screening (e.g., selecting sequence variants with a desired function or properties), and amplification (e.g., creating a new set of sequences for the next iteration). Due to their reliance on a fixed backbone, conventional protein design techniques may be incapable of adopting additional functional constraints even when designing a new protein sequence from scratch (e.g., through Monte Carlo optimization with simulated annealing to make site-specific mutations on the backbone).

Conventional protein design techniques are also inadequate in terms of runtime per task and likelihood of success per prediction. These limitations are counterproductive to successful protein design endeavors, which typically combine computation with very-high-throughput experimental screens that are configured on a case-by-case or function-by-function basis. Although the connection between structural and computational pipelines may be explicit, the connection between protein function and protein structure is far from explicit with conventional protein design techniques. Moreover, with existing protein design techniques, subsequent efforts to design new protein sequences and/or modify existing ones are not informed by the experimental results of previously designed protein sequences. Thus, minimizing the burden on subsequent in vitro and/or in vivo validation through an efficient and precise exploration of the vast protein sequence space to remains a challenge. Accordingly, various aspects of the present disclosure accelerate de novo protein design by providing solutions for more computationally efficient and precise navigation through the aforementioned protein sequence-function space.

In some example embodiments, instead of an indiscriminate exploration of the vast but sparsely populated protein sequence-function space, a protein design engine may generate one or more protein sequences (e.g., sequences of amino acid residues) by sampling a data distribution associated with various known protein sequences. For example, the protein design engine may include a machine learning model that is trained using known protein sequences including protein sequences known to exhibit certain functions and protein sequences without any known functions. In doing so, the machine learning model may learn a data distribution corresponding to a reduced dimension representation of the sequences of amino acid residues forming the known protein sequences. This data distribution may be topological space (e.g., a manifold) occupied by the known protein sequences that describes the relationships between the known protein sequences including, for example, the density of each population of protein sequences exhibiting a similar structure and the magnitude of structural similarities between adjacent populations of protein sequences within the data distribution. Because the high dimensionality of the data associated with the known protein sequences obscures the relationships between populations of protein sequences having structural similarities, the data distribution learned by the machine learning model, which reduces the dimensionality of the data associated with the protein sequences, may enable the identification of one or more populations of protein sequences that exhibit structural similarities.

In some example embodiments, the machine learning model may be a function-conditional generative model that combines a denoising sequence-to-sequence autoencoder with a function analyzer for sampling protein sequences with specific functions (where each sample is a sequence predicted to fold and carry out the target function). For example, the function-conditional generative model can include a transformer-like architecture with a non-autoregressive decoder (NARD) and a function classifier embedded in the architecture. Moreover, the function-conditional generative model can be trained, for example, in a semi-supervised manner, based on approximately 20 million unlabeled protein sequences spanning many evolutionary diverse protein families and approximately 0.5 million protein sequences with known functional labels. Once trained, the function-conditional generative model is capable of making inferences about plausible mutations, insertions, and deletions that are applied to generate one or more output protein sequences from an input protein sequence. Accordingly, the trained function-conditional generative model may be used for sampling new protein sequences from an underlying data distribution (e.g., the manifold) learned through the training. For instance, the sampling of the data distribution (e.g., the manifold) may include a Markov Chain Monte Carlo (MCMC) sampling that iteratively encodes protein sequences into a feature space (or latent space) and decodes from the feature space (or latent space) into protein sequences while leverage the function-based discriminative features of the embedded function classifier. The function guided sampling of the data distribution may significantly improve the computational efficiency associated with de novo protein design while maximizing the diversity and functionality of the resulting protein sequences.

Systems and methods as described herein can navigate through protein sequence-function space more effectively and accelerate protein engineering, such as to provide an explicit connection to function and multiple function profiles, improve performance, and perform multiple design and bioinformatics tasks. For example, protein design and structure can be mapped to multiple functions. A manifold of protein sequences in which protein sequences exhibiting similar and/or identical functions are proximately can be generated and novel protein designs can be generated by interpolating between protein representations on the manifold. The sampling of the manifold thus includes traversing the manifold to identify new protein sequences of variable lengths that exhibit one or more desired functions. Doing so may generate new protein sequences that vary significantly from the starting protein structure. Sparsely annotated functions can be predicted. Conserved sites and salient features on protein sequences can be detected while arbitrary protein scaffolds can be converted to new functions. Multiple objective function objectives can be applied to the procedure for sampling from the manifold and thus multiple functions can be designed on single domains, and functions that are typically found in multiple domains can be integrated into a single domain. Protein sequences can be generated to target a particular function, and redesigned to remove undesired functions.

The aforementioned function-conditional generative model can achieve various features described herein including, for example, sampling highly diverse sequence variants of variable lengths, performing more effective sampling (e.g., due to non-autoregressive decoding procedure employed in its training), and sampling sequences enriched in desired functions (e.g., due to discriminative features extracted from the function classifier). The function-conditional generative model improves upon existing protein design techniques, such as directed evolution approaches, through use of a denoising autoencoder to perform diversification operations and a function classifier for screening. The function-conditional generative model can be used to design protein sequences exhibiting any desired function, which can be evaluated with metrics for sequence similarity, secondary structure, and conformational energy.

FIG. 1A depicts a system diagram illustrating an example of a protein design system 100, in accordance with some example embodiments. Referring to FIG. 1A, the protein design system 100 may include a protein design engine 110, an analysis engine 121, and a client device 130. As shown in FIG. 1, the protein design engine 110, the analysis engine 121, and the client device 130 may be communicatively coupled via a network 145. The client device 130 may be a processor-based device including, for example, a workstation, a desktop computer, a laptop computer, a smartphone, a tablet computer, a wearable apparatus, and/or the like. The network 145 may be a wired network and/or a wireless network including, for example, a local area network (LAN), a virtual local area network (VLAN), a wide area network (WAN), a public land mobile network (PLMN), the Internet, and/or the like.

In some example embodiments, the protein design engine 110 may generate, based on a first protein sequence having a desired function, a second protein sequence having a same (or similar) function. For example, as shown in FIG. 1A, the protein design engine 110 may include a protein design computational model 115. The protein design computational model 115 may be implemented using one or more machine learning models trained to generate the second protein sequence by sampling, based on the first protein sequence, a data distribution learned by the one or more machine learning models during training. The one or more machine learning models may be trained based on a variety of known protein sequences, including protein sequences known to exhibit certain functions and protein sequences without any known functions. In doing so, the one or more machine learning models may learn a data distribution (e.g., a topological space such as a manifold) corresponding to a reduced dimension representation of the sequences of amino acid residues forming the known protein sequences.

In some example embodiments, the protein design computational model 115 may be a function-conditional generative model implemented using an autoencoder (e.g., a denoising sequence-to-sequence autoencoder (DAE) and/or the like) with a non-autoregressive decoder (NARD). Accordingly, the protein design computational model 115 may learn the data distribution by learning to generate an encoding of an input protein sequence that can be decoded to form an output protein sequence that is minimally different from the input protein sequence. At inference time, the data distribution associated with the trained protein design computational model 115 may be sampled by encoding a first protein sequence exhibiting a desired function before decoding an intermediate sequence having at least one of a corruption (e.g., an insertion, a deletion, and/or a modification of an amino acid residue) or a length change relative to the first protein sequence. Moreover, the sampling of the data distribution may include decoding the intermediate sequence to generate a second protein sequence that is different than the first protein sequence but is still likely to exhibit a same (or similar) function as the first protein sequence.

Each sampling of the data distribution may correspond to a single sampling iteration generating at least one candidate protein sequence for subsequent structural and/or functional analysis, for example, by the analysis engine 121. The protein design engine 110 may continue to sample the data distribution until one or more conditions are satisfied including, for example, the identification of a threshold quantity of candidate protein sequences, the identification of a threshold quantity of protein sequences exhibiting a desired function, and/or the like. It should be appreciated that the protein design engine 110 may apply a variety of techniques to sample from the data distribution including, for example, a Markov Chain Monte Carlo (MCMC), importance sampling (IS), rejection sampling, Metropolis-Hastings, Gibbs sampling, slice sampling, exact sampling, and/or the like. Moreover, as shown in FIG. 1A, the analysis engine 121 may analyze the second protein sequence by performing one or more of a function prediction 123 (e.g., to determine one or more functions of the second protein sequence), structural modeling 125 (e.g., to determine a secondary structure and/or a tertiary structure of the second protein sequence), and molecular dynamics simulations 127 (e.g., to determine an energy state and stability of the second protein sequence). At least a portion of the results associated with the sampling, the functional analysis, and/or the structural analysis may be provided for display, for example, in a user interface 135 at the client device 130.

In some example embodiments, when implemented as an autoencoder (e.g., a denoising autoencoder (DAE) and/or the like, the protein design computational model 115 may include a corruption process $C(\tilde{L}|L)$, an encoder F, and a decoder G. Moreover, the protein design computational model 115 may include a length predictor, which may be implemented as a classifier configured to output a categorical distribution over the possible length differences between an input protein sequence and an output protein sequence. The protein design computational model 115 may operate on a sequence of discrete tokens forming the input protein sequence, $x=(x_1, x_2, \ldots, x_L)$, wherein each token $x_t$ is an item from a finite vocabulary V.

When applied towards protein design, the vocabulary V may include the amino acid residues that be present in a protein sequence such as the 22 proteinogenic amino acids or the 20 amino acids of the genetic code. The input protein sequence x is corrupted with the corruption process C, resulting in a corrupted sequence $\tilde{L} \sim C(\tilde{L}|L)$. The corruption process C associated with the protein design computational model 115 can be arbitrary as long as it is largely local and unstructured. In some cases, the corruption process C may even alter the length of the sequence such that $|L| \neq |\tilde{L}|$.

The encoder F can be implemented using a variety of deep learning architectures including, for example, transformers, convolutional neural networks, recurrent neural networks, and/or the like. The encoder F turns the corrupted sequence $\tilde{L}$ into a set of hidden vectors, $h=(h_1, h_2, \ldots, h_{|\tilde{L}|})$, wherein each hidden vector $h_t \in \mathbb{R}^d$. In some cases, the hidden vectors h are pooled to form a single-vector representation $$\bar{h} = \frac{1}{|\tilde{L}|} \sum_{t=1}^{|\tilde{L}|} h_t.$$

This pooled single-vector representation h is used by the length converter to predict the change in length between the input protein sequence and the output protein sequence. In some cases, the length converter may be a machine learning model that is trained to output a predicted length change dL where $dL^* = |\tilde{L}| - |L|$. When the trained machine learning model samples from the data distribution during inference time, the predicted length change dL may be applied to adjust the size of the hidden vector set h with the adjusted hidden vector set having an $|\tilde{L}|+dL$ number of hidden vectors, thus generating a transformed hidden vector sequence $z=(z_1, \ldots, z_{|\tilde{L}|+dL})$, wherein $z_t = \sum_{t'=1}^{|\tilde{L}|} \omega_{t,t'} h_{t'}$, and $$\omega_{t,t'}^t \propto \exp\left(-\beta \left|\frac{t}{|\tilde{L}|+dL} - \frac{t'}{|\tilde{x}|}\right|\right).$$

The decoder G then takes this transformed hidden vector sequence z and outputs a corresponding sequence of logit vectors, $\tilde{y}=(\tilde{y}_1, \ldots, \tilde{y}_{|\tilde{L}|+dL})$, wherein each logit vector $\tilde{y}_t \in \mathbb{R}^{|v|}$. These logit vectors y can be turned into probability distributions over the vocabulary V in many different ways. One example technique is a non-autoregressive approach in which each logit vector $\tilde{y}_t$ is turned independently into a distribution $$p(y_t = v | \tilde{L}, dL) = \frac{\exp(\tilde{y}_t^v + b^v)}{\sum_{v' \in V} \exp(\tilde{y}_t^{v'} + b^{v'})},$$

wherein $b^v$ denotes a bias for the token v. Alternative techniques for turning the logit vectors $\tilde{y}$ into probability distributions over the vocabulary V include conditional random fields, autoregressive modeling, and/or the like.

During training of the protein design computational model 115, the encoder F may be trained to generate, based on a corrupted version of the input protein sequence, an encoding of the input protein sequence that enables the decoder G to generate a decoding that exhibits a minimal difference relative to the original, uncorrupted version of the input protein sequence. That is, during training, the encoder F and the decoder G may be trained by minimizing the negative log-probability of the original sequence L given the corrupted version $\tilde{L}$ and a known length change dL*, while the negative log-probability of the known length change dL* is applied towards training the length converter. Once training of the protein design computational model 115 is complete, one or more candidate protein sequences may be drawn from the protein design computational model 115, for example, by repeating the process of corruption, length conversion, and reconstruction over several sampling iterations (e.g., Markov Chain Monte Carlo (MCMC) sampling iterations and/or the like).

Figure 1B:
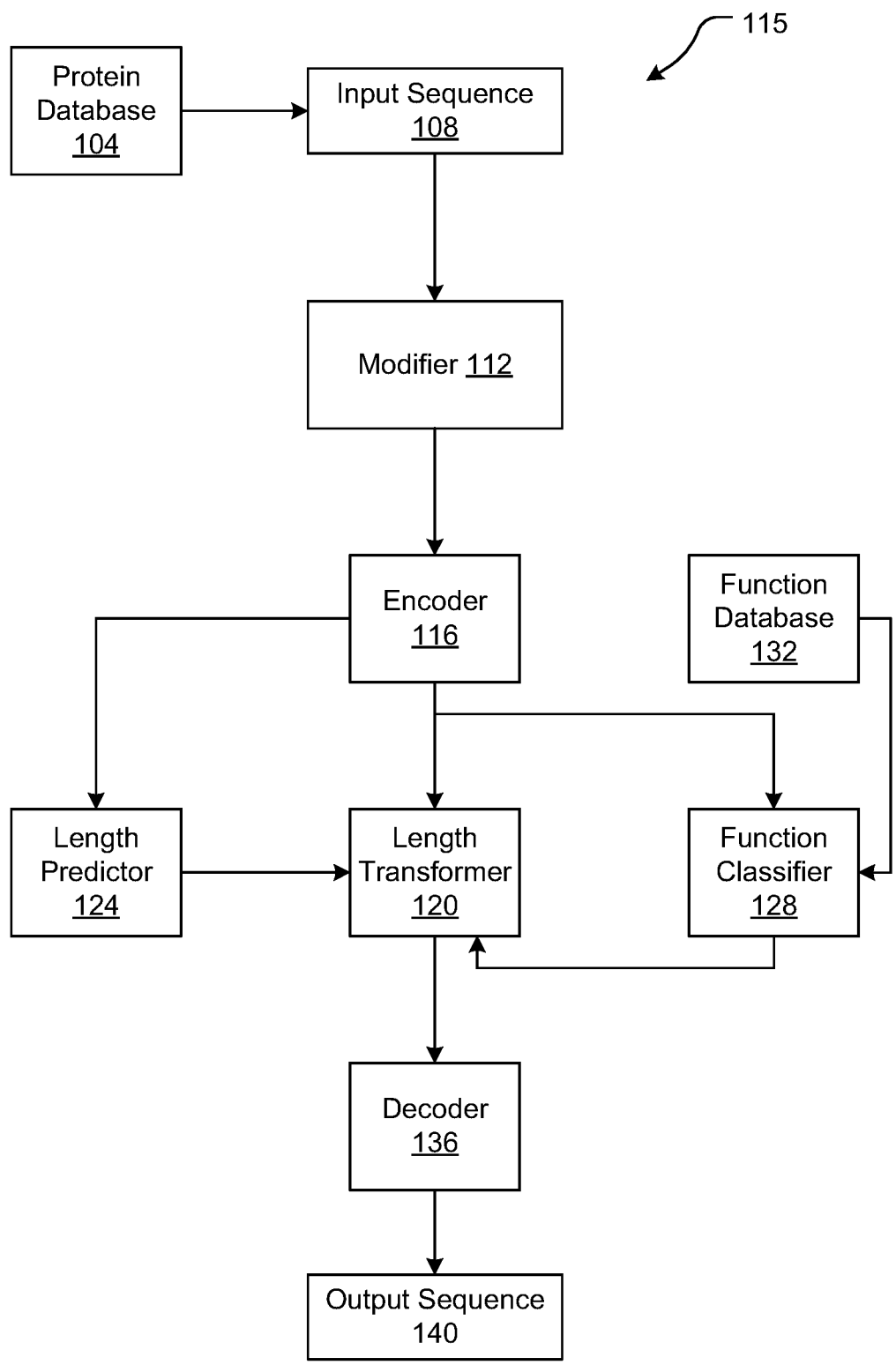
FIG. 1B depicts a block diagram illustrating an example of a protein design computational model, in accordance with some example embodiments.

To further illustrate, FIG. 1B depicts a block diagram illustrating an example of the protein design computational model 115 that can be used to implement various features and functions described herein. In some example embodiments, the protein design computational model 115 can be implemented using one or more machine learning models (e.g., a denoising sequence-to-sequence autoencoder (DAE) with a non-autoregressive decoder (NARD)) that are trained to generate protein sequences expected to achieve certain desired functions. For example, the protein design computational model 115 may generate one or more output protein sequences exhibiting a desired function based on an input protein sequence without the desired function due to a lack of corresponding structures (e.g., primary, secondary, and/or tertiary protein structures). The protein design computational model 115 may be trained to modify protein sequences into those exhibiting the desired function by at least learning to revert randomly modified (e.g., mutated) protein sequences back to the original, non-modified protein sequences (e.g., to a version having similar or identical structure or function). As described in more detail below, at least some components of the protein design computational model 115 may be implemented to include one or more stacked multi-head attention (MHA) layers.

Referring again to FIG. 1B, the protein design computational model 115 may include or be communicatively coupled with a protein database 104. The protein database 104 can maintain protein data structures representative of proteins. For example, each protein data structure can correspond to a protein, and can include one or more elements identifying a respective amino acid of a sequence of amino acids (e.g., residues) corresponding to the protein. The sequence of amino acids can represent a polypeptide chain, for example, with each element of the protein data structure representative of an amino acid residue and having one or more links to one or more adjacent elements representative of adjacent amino acid residues. In some cases, the protein data structures included in the protein database 104 may indicate secondary structures (e.g., alpha helices, beta sheets) of the protein.

As shown in FIG. 1B, the protein design computational model 115 may receive at least one input sequence 108. The input sequence 108 may correspond to a protein sequence (e.g., a sequence of amino acid residues) retrieved from the protein database 104 and/or determined based on one or more user inputs received from the client device 130. In some example embodiments, the input sequence 108 can be selected or generated to be relatively distant from a desired function. That is, the input sequence 108 may not be expected to exhibit the desired function. For example, the input sequence 108 can include one or more randomly selected residues. Alternatively and/or additionally, the input sequence 108 can have at least a predetermined difference from a predetermined function assignment of a target protein sequence. In some cases, the input sequence 108 can have a below-threshold function classification score for the desired function. Providing such an input sequence to the protein design computational model 115 may trigger a search of a previously unsearched portion of the topological space (e.g., manifold) representative of the protein sequence-function space to uncover novel structures capable of performing the desired function.

Referring again to FIG. 1B, the protein design computational model 115 can include a modifier 112 configured to modify the input sequence 108 to generate a modified protein sequence. For example, the modifier 112 can modify the input sequence 108 by changing the sequence of amino acid residues represented by the corresponding protein data structure. In some cases, the modifier 112 can change the sequence of amino acid residues by applying at least one of a corruption (e.g., an insertion, a deletion, and/or a modification of an amino acid residue) and a length change. Accordingly, where the modifier 112 receives the input sequence 108 having an length L (e.g., a sequence of amino acid residues having an L quantity of positions), the output of the modifier 112 may be a corrupted or noisy version of the input sequence 108 of a different length $\tilde{L}$. For example, the modifier 112 can perform a function $C(\tilde{X}|X)$, where $X$ denotes the input sequence 108 and $\tilde{X}$ denotes the modified sequence output by the modifier 112.

To generate the modified sequence $\tilde{X}$, the modifier 112 can modify (e.g., insert, delete, change) a particular quantity of amino acid residues in the input sequence X. The quantity of amino acid residues in the input sequence X that undergo modification can be a predetermined value, such as a predetermined number less than or equal to 10. Alternatively, the quantity of amino acid residues in the input sequence X that are modified by the modifier may be a randomly generated value, such as a randomly selected number less than or equal to 10 (or greater than or equal to −10 and less than or equal to 10, where negative values can correspond to removal of residues).

The modifier 112 can selectively identify amino acid residues for modification based on one or more external parameters (e.g., external factor, external signal, external constraint). For example, the modifier 112 can selectively modify certain amino acid residues specified by the external parameter. Alternatively and/or additionally, the external parameter may specify certain amino acid residues for conservation, in which case the modifier 112 may be prevented from modifying these amino acid residues.

The modifier 112 can modify the input sequence X by deleting one or more amino acid residues, including deleting a particular quantity of amino acid residues, by identifying (e.g., randomly identifying, selectively identifying, and/or the like) one or more amino acid residues for deletion and outputting a modified protein data structure in which the identified amino acid residues are deleted.

In addition to and/or instead of deleting one or more amino acid residues, the modifier 112 can modify the input sequence X by inserting one or more amino acid residues. For example, the modifier 112 can insert a particular quantity of amino acid residues. Moreover, to insert the one or more amino acid residues, the modifier 112 can identifying (e.g., randomly identifying, selectively identifying, and/or the like) one or more positions between existing amino acid residues in the original input sequence X for inserting the one or more amino acid residues. The modifier 112 may output a modified protein data structure in which the one or more amino acid residues have been inserted at the one or more positions. It should be appreciated that the amino acid residues inserted into the input sequence X can be selected, for example, randomly, from the 22 proteinogenic amino acids, or the 20 amino acids of the genetic code.

In addition to and/or instead of the deleting and inserting of amino acid residues, the modifier 112 can modify the input sequence X by modifying one or more existing amino acid residues in the input sequence X. This modification may be applied to a particular quantity of amino acid resides in the input sequence X. For example, the modifier 112 can identify (e.g., randomly identify, selectively identify, and/or the like) one or more amino acid residues in the input sequence X for modification. The modification of an amino acid residue in the input sequence X may include replacing the existing amino acid residue with a different amino acid residue selected, for example, randomly, from the 22 proteinogenic amino acids, or the 20 amino acids of the genetic code.

Referring again to FIG. 1B, the protein design computational model 115 can include an encoder 116. The encoder 116 can determine a mapping from a protein sequence space (e.g., corresponding to the features of the protein data structures, such as the input sequence 108 or modified protein data structures) to a latent space (e.g., a position or set of positions on the manifold). For example, the encoder 116 can map the modified protein data structure, having the length $\tilde{L}$ and including an encoding of the constituent amino acid residues (e.g., one-hot encoding and/or the like) $\tilde{x}_1, \ldots, \tilde{x}_{\tilde{L}} \in [0,1]^{\tilde{L} \times 22}$, to a sequence of continuous amino acid representations $\tilde{Z}=\tilde{z}_1, \ldots, \tilde{z}_{\tilde{L}} \in \mathbb{R}^{\tilde{L} \times d}$, where the embedding dimension is denoted by d. For example, the encoder 116 can perform a function $Q_\theta(\tilde{Z}|\tilde{X})$ for the mapping from protein sequence space to latent space, where θ is a learnable set of parameters for the encoder 116.

Figure 2:
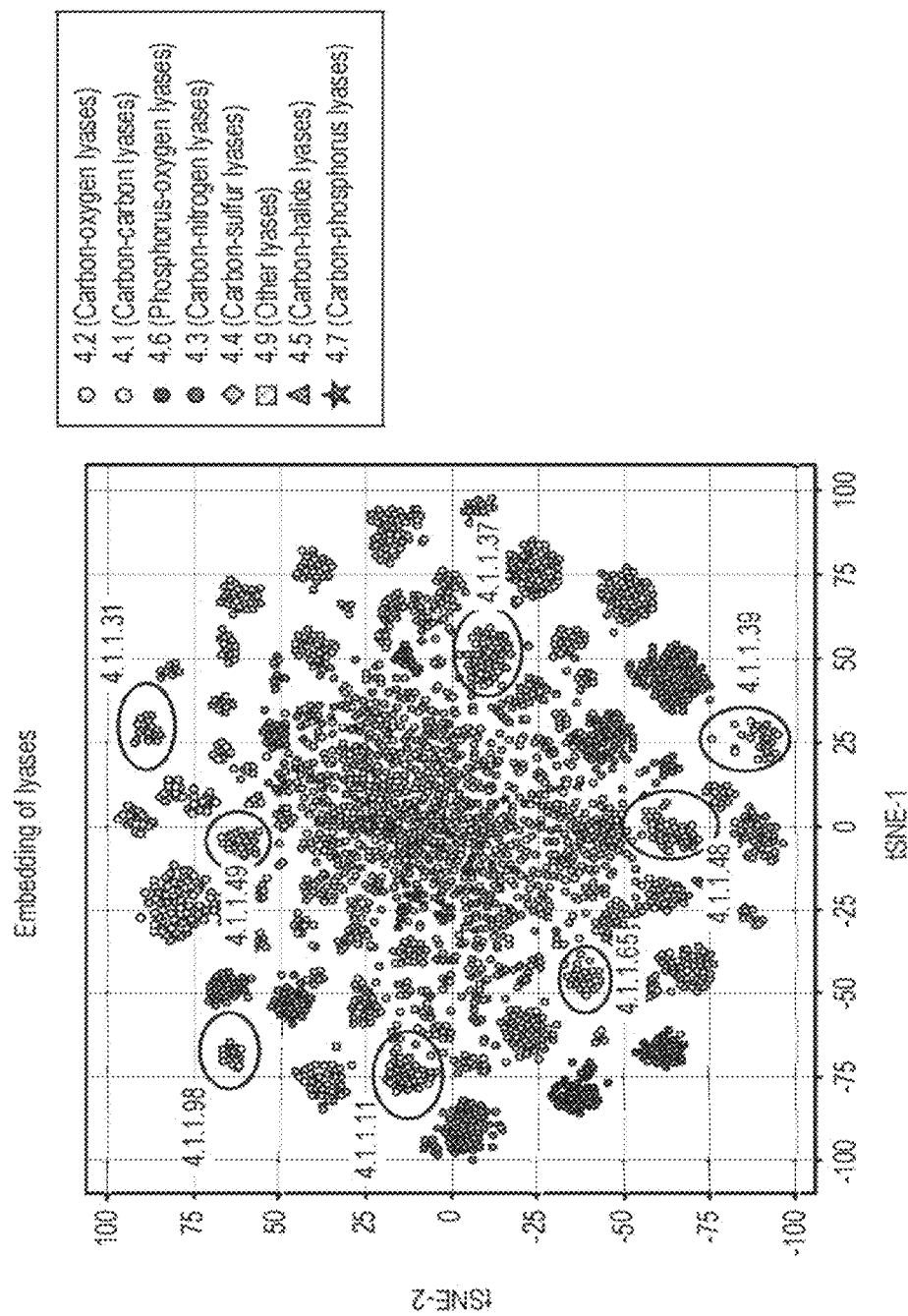
FIG. 2 depicts a chart illustrating an example of a t-distributed stochastic neighbor embedding (t-SNE) of protein lyases, in accordance with some example embodiments.

By using the encoder 116 to map the modified protein data structure to the latent space (e.g., a feature space in which sequences having similar functions can be relatively close to one another, such as being positioned in clusters, an example of which is depicted in FIG. 2), the protein design computational model 115 can sample various protein representations in a manner that is more efficient and more attuned to sampling to achieve the desired functions (e.g., relative to modifying the input sequence X in the amino acid sequence space, where it can be more difficult to determine how modifying amino acids leads to corresponding changes in function).

As shown in FIG. 1B, the protein design computational model 115 can include a length transformer 120. The length transformer 120 can be used to transform the sequence of continuous amino acid representations $\tilde{Z}$ having the length $\tilde{L}$ (which may be different from the length L of the original input sequence X depending on whether the modifier 112 inserted or removed residues from the input sequence X) into an L quantity of latent vectors. For example, the length transformer 120 can apply a monotonic location-based attention mechanism to perform a transform operation $f_\omega(Z|\tilde{Z}, \Delta L)$, which can receive the latent representation $\tilde{Z}$ and a length difference $\Delta L$ between the lengths L and $\tilde{L}$, and output a modified representation $\tilde{Z}$ having an adjusted length of L (e.g., adjusted from the length $\tilde{L}$). The modified representation Z can be generated as $Z=z_1, \ldots, z_L$, wherein each $z_i$ is determined as a weighted sum of the amino acid latent representations (e.g., vectors) from the encoder 116 and $a_j^i$ denote the attention coefficients.

The protein design computational model 115 can include a length predictor 124. The length predictor 124 can determine the length difference between the output sequence 140 and the modified protein sequence (e.g., predict ΔL), such as when the protein design computational model 115 is used to generate the output sequence 140 to exhibit a desired function. For example, the length predictor 124 can be represented as $P_\eta(\Delta L|\tilde{Z})$, such as a classifier that outputs a categorical probability of the length difference. The length predictor 124 can be trained simultaneously with other components of the protein design computational model 115 (e.g., one or more denoising autoencoder components such as the modifier 112, the encoder 116, the decoder 136, and the length transformer 120). The length predictor 124 can receive, as input, a protein-level representation generated by averaging the amino acid representation, and output a categorical distribution that represents a range of length differences, $[-\Delta L_{max}, \Delta L_{max}]$, where $\Delta L_{max}$ is dependent upon the corruption process applied by the modifier 112. The length predictor 124 can be parameterized by a single fully connected layer having a softmax output. The length transformer 120 can receive the length difference ΔL determined by the length predictor 124 to perform the length transformation.

Referring again to FIG. 2, the protein design computational model 115 can include a function classifier 128. The function classifier 128 can be trained to identify one or more functions exhibited by the protein sequences sampled from the manifold learned by the protein design computational model 115. In some cases, the function classifier 128 may be configured to perform one or more of the analysis associated with the analysis engine 121 including, for example, function prediction 123, structural modeling 125, and molecular dynamics simulations 127. The output of the function classifier 128 can enable the protein design computational model 115 to have function-specific discriminative features to facilitate generating protein sequences exhibiting certain desired functions and/or lacking certain undesired functions. For example, where the output of the function classifier 128 indicates that a protein sequence sampled from the manifold exhibits a desired function and/or an undesired function, the protein design computational model 115 may continue to iterate through modifications of the original input sequence X until one or more protein sequences exhibiting the desired function and/or lacking the undesired function is sampled from the manifold.

In some example embodiments, the function classifier 128 may be implemented as a multi-label classifier, such as a classifier defined as $P_\omega(Y|\tilde{Z})$. In some cases, the function classifier 128 may be trained based on protein sequences labeled with the known functions of each protein sequence. Once trained, the function classifier 128 can receive, from the encoder 116, the latent sequence representation $\tilde{Z}$ (e.g., initial sequence feature representation), and output a function probability vector Y and one or more internal states $Z_c$ of the function classifier 128. The classifier $P_\omega$ can be parameterized as a multi-head attention (MHA) layer that maps the initial sequence feature representation Z to an internal feature representation $\tilde{Z}_c$ having a same hidden dimension as having a same hidden dimension as the latent sequence representation $\tilde{Z}$. The internal feature representation $\tilde{Z}_c$ can be pooled to form a protein-level representation $$z_c^{pool} = \frac{1}{L}\sum_{i=1}^{L} \tilde{z}_{ci}.$$

This protein-level representation $z_c^{pool}$ can be passed to a single fully connected layer followed by an activation function (e.g., a point-wise sigmoid function) that returns, for each possible function, a probability that the protein sequence having the latent sequence representation $\tilde{Z}$ exhibits the function.

Referring again to FIG. 2, the protein design computational model 115 can include the decoder 136, which perform the decoding function $P_\varphi(X|Z)$ to generate the output sequence 140 corresponding to the input sequence 108. For example, the decoder 136 can generate the output sequence 140 by at least decoding the length transformed output Z of the length transformer 120. The decoder 136 can predict the probability of the target tokens in order to generate the at least one output sequence 140. For example, the decoder 136 may take the transformed hidden vector sequence z from the length transformer 120 and output a corresponding sequence of logit vectors, $\tilde{y}=(\tilde{y}_1, \ldots, \tilde{y}_{\mathrm{lxl}+\Delta l})$, wherein each logit vector $\tilde{y}_t \in R^{|v|}$. These logit vectors $\tilde{y}$ can be turned into probability distributions over the vocabulary V (e.g., of the 22 proteinogenic amino acids or the 20 amino acids of the genetic code) in a variety of ways. For instance, the decoder 136 may be a non-autoregressive decoder (NARD), in which case each logit vector $\tilde{y}_t$ is turned independently into a distribution $$p(y_t = v|\tilde{x}, \Delta l) = \frac{\exp(\tilde{y}_t^v + b^v)}{\Sigma_{v' \in V}\exp(\tilde{y}_t^{v'} + b^{v'})},$$

wherein $b^v$ denotes a bias for the token v. Alternative techniques for turning the logit vectors $\tilde{y}$ into probability distributions over the vocabulary V include conditional random fields, autoregressive modeling, and/or the like.

While performing inference processes (e.g., using the trained protein design system 100 to modify the input sequence 108 into the output sequence 140 having high scores for the Desired functions), the function classifier 128 can determine a gradient of the input representation, Z, for the desired functions of the output sequence 140. The gradient can represent changes of function scores or probabilities in the feature space, such as to indicate how modifications to the input representation in the feature space can result in changes in the functions exhibited by the output sequence 140. For example, the desired functions can be indicated by gene ontology terms (e.g., terms from the Gene Ontology database as described with reference to FIG. 3 below), such that the gradient represents a gradient of probability of gene ontology term labels. The gradient (e.g., output of the function classifier 128) can be defined by Equation (1) below.

$$\nabla_Z^t = \frac{\partial P_W(Y=Y_i|Z)}{\partial \tilde{Z}} \tag{1}$$

The length transformer 120 can perform length transformation on the input representation and the gradients, such that the gradients can be expected to increase the fitness of the output sequence 140 generated by the decoder 136 (e.g., based on the length transformed output of the length transformer 120 that is generated using the gradients).

The protein design computational model 115 can store associations between the output sequence 140 and functions identified for the output sequence 140. For example, the protein design system 100 can store or output associations between function assignments that the function classifier 128 detects for the protein sequence or sequence of amino acid residues corresponding to the output sequence 140. The function classifier 128 can receive the output sequence 140, detect one or more functions of the output sequences, and assign the detected functions to the output sequence 140.

To train the underlying machine learning models of the protein design computational model 115, such as the encoder 116, length transformer 120, the length predictor 124, the function classifier 128, and the decoder 136 (e.g., to determine the model parameters θ of the encoder 116, φ of the decoder 136, η of the length predictor 124, ω of the function classifier 128, and σ of the length transformer 120), the protein design computational model 115 can use a training data set that includes at least one predefined input sequence 108 (e.g., sequence x) and target sequence (e.g., sequence y), having predefined lengths $l_x$, $l_y$, respectively. Given a protein-level embedding vector, $z_{pool}$, the underlying machine learning models are trained to predict the length difference between $l_y$ and $l_x$. For example, the probability $p(l_y-l_x|z_{pool})$ can be modeled as a softmax probability distribution that covers the length difference $[-(p/100)*L_{max}, (p/100)*L_{max}]$, where $L_{max}$ is a maximum sequence length in the entire training set.

Figure 8:
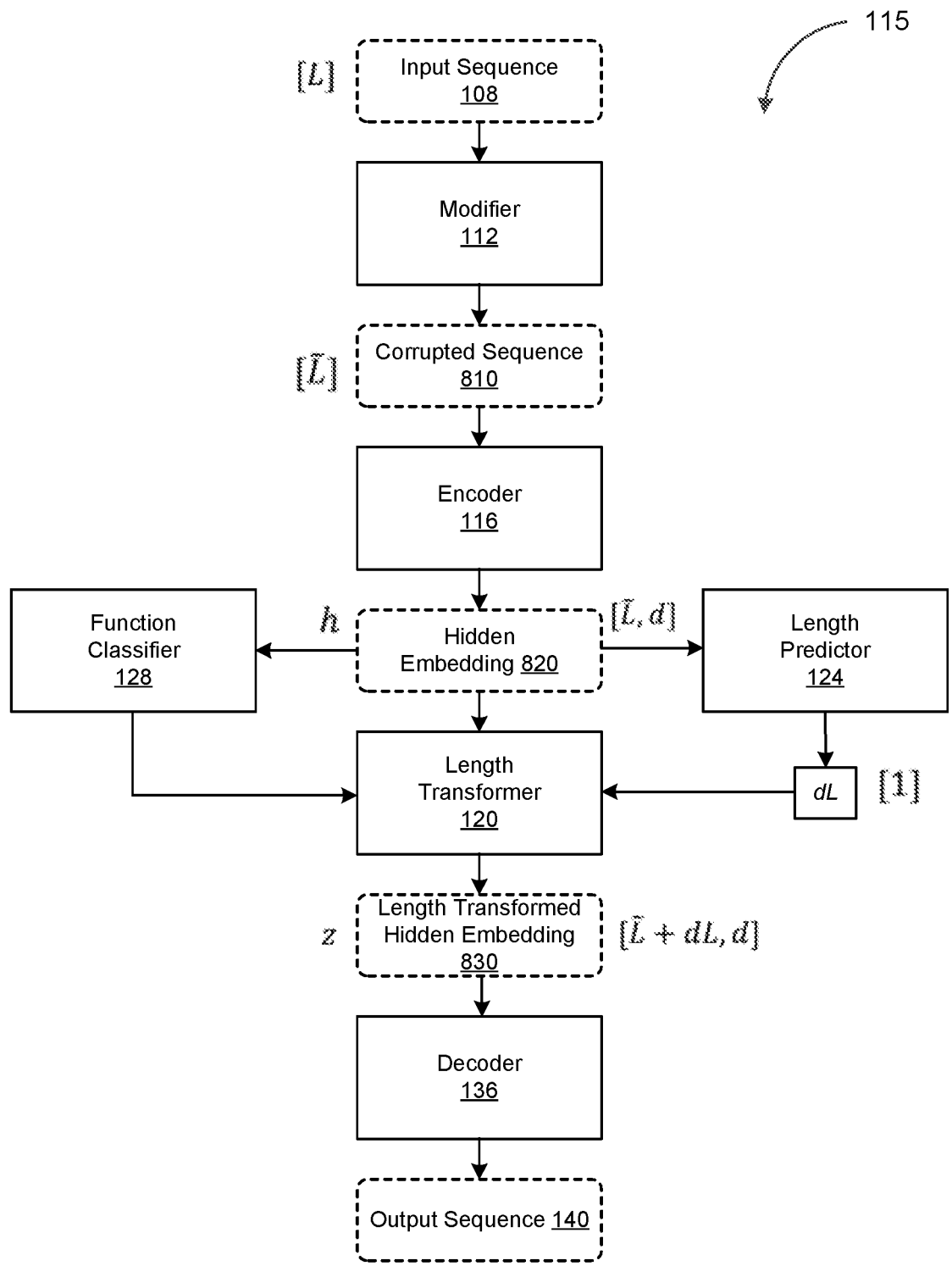
FIG. 8 depicts a block diagram illustrating an example of data flow within a protein design computational model, in accordance with some example embodiments.

FIG. 8 depicts a block diagram illustrating an example of data flow within the protein design computational model 115, in accordance with some example embodiments. As noted, the protein design computational model 115 may be configured to generate the output sequence 140 based on the input sequence 108. For example, the protein design computational model 115 may generate the output sequence 140 by at least applying, to the input sequence 108, one or more corruptions that include inserting an amino acid residue into the input sequence 108, deleting an amino acid residue from the input sequence 108, and/or modifying an amino acid residue present in the input sequence 108. In some example embodiments, the output sequence 140 may be generated by sampling the data distribution associated with the trained protein design computational model 115. For instance, the sampling of the data distribution may include encoding the input sequence 108 before decoding an intermediate sequence having at least one of a corruption (e.g., an insertion, a deletion, and/or a modification of an amino acid residue) or a length change relative to the first protein sequence. Moreover, the sampling of the data distribution may include decoding the intermediate sequence to generate the output sequence 140, which may be different than the input sequence 108. In some cases, the output sequence 140 may be generated to exhibit one or more of the same desired functions as the input sequence 108. Alternatively and/or additionally, the output sequence 140 may be generated to include one or more desired functions that are not present in the input sequence 108 and/or to exclude one or more undesired functions that are present in the input sequence 108.

Referring to FIGS. 1B and 8, the modifier 112 of the protein design computational model 115 may receive the input sequence 108, which may be a protein sequence [L] having an L quantity of amino acid residues. To generate the output sequence 140, the modifier 112 may operate on the input sequence 108 to generate a corrupted sequence 810 having an $\tilde{L}$ quantity of amino acid residues, where the $\tilde{L}$ quantity of amino acid residues is not necessarily the same quantity as the L quantity of amino acid residues in the input sequence 108. The corrupted sequence 810 may be encoded, for example, by the encoder 116, to generate a hidden embedding 820, which may be a set of hidden vectors, $h=(h_1, h_2, \ldots, h_{|\tilde{L}|})$, wherein each hidden vector $h_i \in \mathbb{R}^d$. As shown in FIG. 8, the hidden embedding 820 may include an $\tilde{L}$ quantity of vectors, each of which having a dimension of d.

As will be described in more detail, the length predictor 124 may determine, based at least on this hidden embedding 820, a length change dL. The length transformer 120 may apply the length change dL to generate a length transformed hidden embedding 830, which may be a set of vectors $z=(z_1, z_2, \ldots, z_{|\tilde{L}+dL|})$. That is, the length transformer 120 may output an $\tilde{L}+dL$ quantity of vectors, each of which having a dimension of d. As shown in FIG. 8, the decoder 136 may decode the length transformed hidden embedding 830 in order to generate the output sequence 140. In some example embodiments, the generating of the length transformed hidden embedding 830 may be conditioned on the functions associated with the length transformed hidden embedding 830. For instance, as shown in FIG. 8, the function classifier 128 may be trained to identify one or more of the functions present in a protein sequence associated with the length transformed hidden embedding 830. That is, the function classifier 128 may operate on the latent space representation of a candidate protein sequence and not the protein sequence space representation of the protein sequence in order to facilitate the traversal of the topological space (e.g., manifold) learned by the protein design computational model 115 during initial training. Thus, the traversal of the topological space (e.g., manifold) for subsequent sampling iterations (e.g., Markov Chain Monte Carlo (MCMC) sampling iterations) may be guided at least in part by the desirable and/or undesirable functions present in the protein sequence associated with the length transformed hidden embedding 830.

Figure 9A:
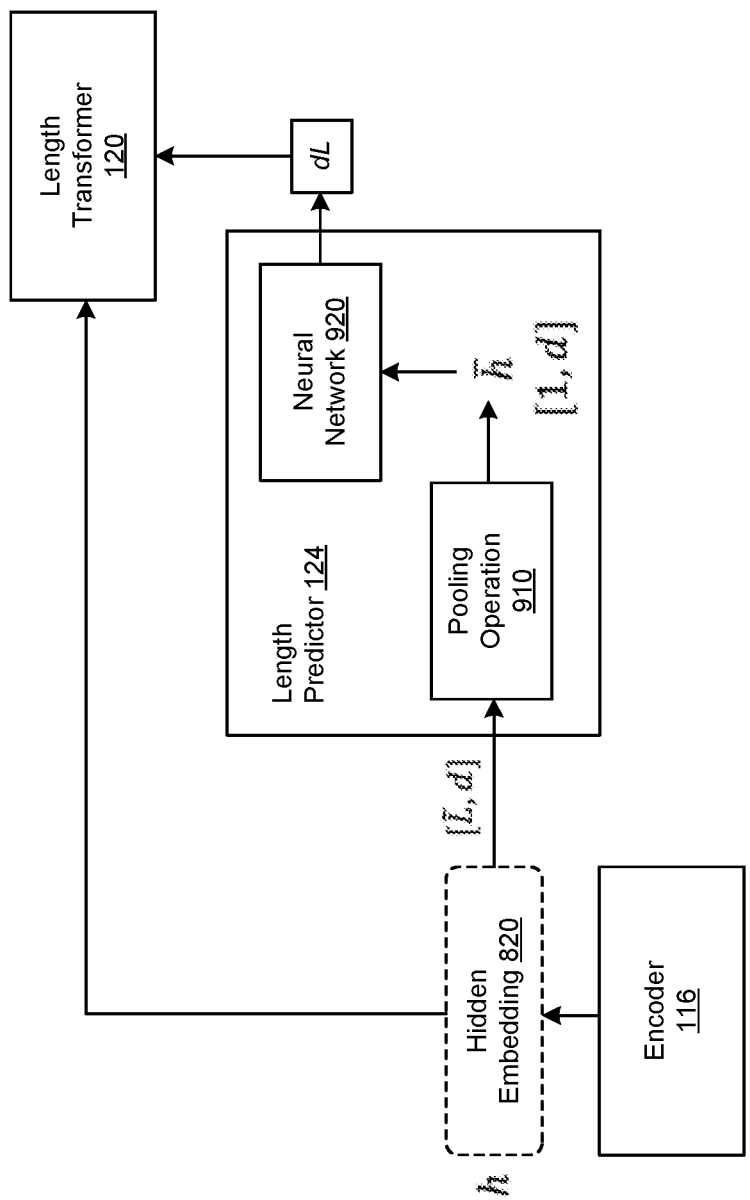
FIG. 9A depicts a block diagram illustrating an example of a length predictor, in accordance with some example embodiments.

As noted, in some example embodiments, the protein design computational model 115 may include the length predictor 124 a length change that can be applied to generate the output sequence 140. The length predictor 124 may be implemented in a variety of ways. FIG. 9A depicts a block diagram illustrating one example of the length predictor 124, in accordance with some example embodiments. In some cases, the length predictor 124 may determine the length change dL by performing a pooling operation 910 (e.g., an average pooling operation) on the hidden embedding 820. As noted, the hidden embedding 820 may include a set of hidden vectors, $h=(h_1, h_2, \ldots, h_{|\tilde{L}|})$, each of which having a dimension of d. Applying the pooling operation 910 on the hidden embedding 820 may compress the $\tilde{L}$ quantity of vectors in the hidden embedding 820 into a single, d-dimensional vector representation $\bar{h}$. A machine learning model, such as a neural network 920, may be applied to this single, d-dimensional vector representation $\bar{h}$ to determine the length change dL. For instance, the neural network 920 may be trained as a classifier to output a categorical distribution of the possible length changes between the input sequence 108 and the output sequence 140 (e.g., within a maximum range of possible length differences $[-\Delta L_{max}, \Delta L_{max}]$ in which $\Delta L_{max}$ is contingent upon the corruption process applied by the modifier 112).

Figure 9B:
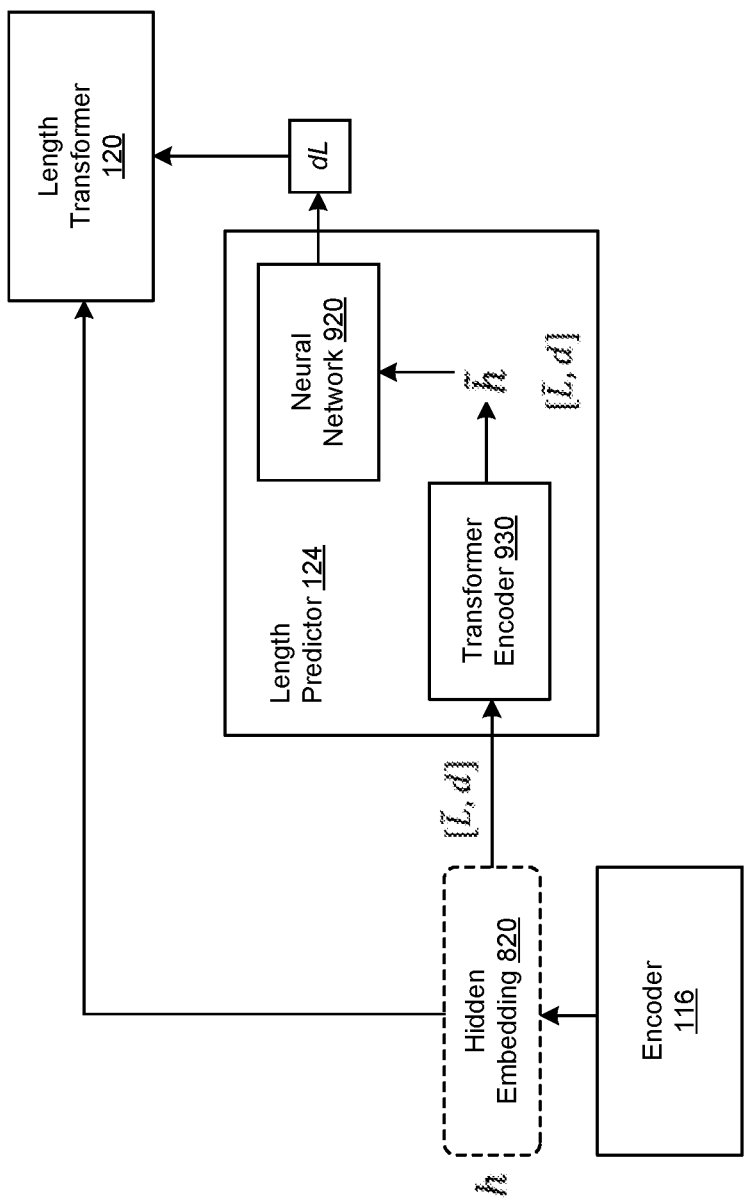
FIG. 9B depicts a block diagram illustrating another example of a length predictor, in accordance with some example embodiments.

Another example of the length predictor 124 for determining the length change for generating the output sequence 140 is shown in FIG. 9B. Referring to FIG. 9B, in some example embodiments, the length predictor 124 may be implemented as a transformer encoder 930 instead of the pooling operation 910 (e.g., a mean pooling operation).

Doing so may preserve more of the information present in the $\tilde{L}$ quantity of vectors forming the hidden embedding 820 during the length prediction process, whereas applying the pooling operation 910 compresses the $\tilde{L}$ quantity of vectors into a single, d-dimensional vector representation $\bar{h}$.

In some example embodiments, the transformer encoder 930 may be the encoder stack of a transformer deep learning model that also includes a decoder stack coupled to the output of the encoder stack. The encoder stack of the transformer model may include one or more encoding layers whereas the decoder stack of the transformer model may include one or more decoding layers. Each encoding layer in the encoder stack may be configured to generate encodings that contain information about which parts of the inputs are relevant to each other. The output of one encoding layer may be passed on as the input of a subsequent encoding layer. Contrastingly, each decoding layer may generate, based on each of the encodings output by the encoder stack and the corresponding contextual information, an output sequence. The encoding and decoding layers of the transformer model may apply one or more attention mechanisms in order to provide contextual information for their respective inputs. For example, the final layer of the encoder stack may include an attention mechanism to draw information from each encoding into a single vector that concentrates information from the other encodings, which are also output by the encoder stack as corresponding vectors. Each decoding layer may include additional attention mechanisms to draw information from the outputs of preceding decoding layers, before the decoding layer draws information from the encodings received from the encoding stack.

Referring again to FIG. 9B, due to the attention mechanisms applied by the transformer encoder 930, the output of the transformer encoder 930 may be an encoding $\tilde{h}$ that pools information from a select subset of vectors $h=(h_1, h_2, \ldots, h_{|\tilde{L}|})$. This encoding $\tilde{h}$, which includes an $\tilde{L}$ quantity of d-dimensional vectors, may be more representative of the information conveyed in the original hidden embedding 820 than the single, d-dimensional vector representation $\bar{h}$ generated by applying the pooling operation 910. As shown in FIG. 9B, the encoding $\tilde{h}$ may be passed to the neural network 920, which may determine, based at least on the encoding $\tilde{h}$, a categorical distribution of the possible length changes between the input sequence 108 and the output sequence 140. For example, in some cases, the neural network 920 may operate on a single vector from the encoding $\tilde{h}$ (e.g., the first vector from the encoding $\tilde{h}$) that concentrates information from the other vectors in the encoding $\tilde{h}$. Alternatively, the neural network 920 may operate on each one of the $\tilde{L}$ quantity of d-dimensional vectors in the encoding $\tilde{h}$, in which case the output of the neural network 920 for each of the vectors (e.g., an individual categorical distribution of possible length changes may be determined for each vector in the encoding $\tilde{h}$) may undergo additional operations (e.g., averaged) to determine the length change dL. The resulting length change dL may be within a maximum range of possible length differences $[-\Delta L_{max}, \Delta L_{max}]$ in which $\Delta L_{max}$ is contingent upon the correction process applied by the modifier 112.

Figure 10A:
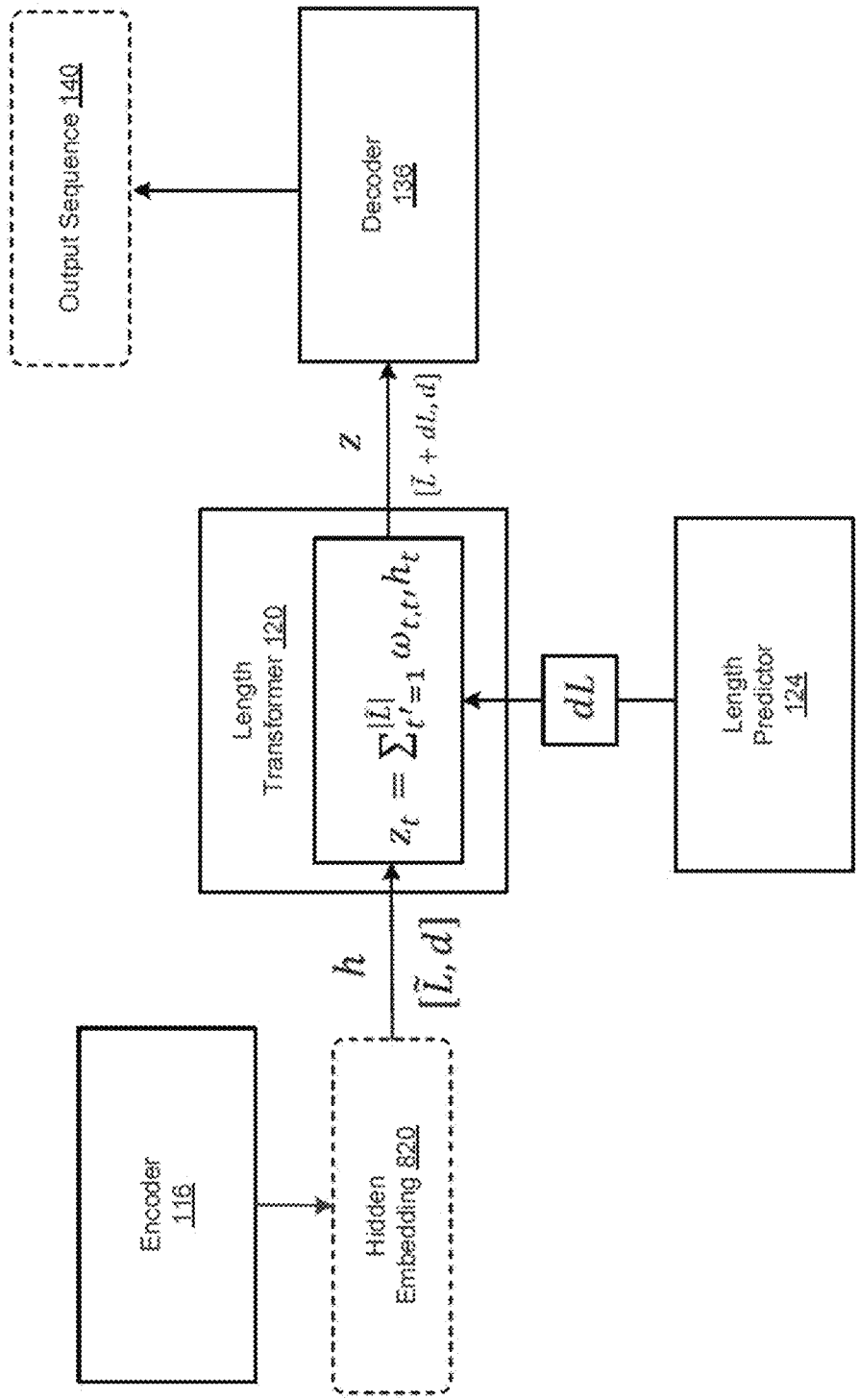
FIG. 10A depicts a block diagram illustrating an example of a length transformer, in accordance with some example embodiments.

As noted, in some example embodiments, to generate the output sequence 140, the protein design computational model 115 may include the length transformer 120, which applies the length change determined by the length predictor 124. The length transformer 120 may be implemented in a variety of different ways. FIG. 10A depicts a block diagram illustrating one example of the length transformer 120, in accordance with some example embodiments. As shown in FIG. 10A, in some cases, the length transformer 120 may operate by applying, to the hidden embedding 820 generated by the encoder 116 and the length change dL determined by the length predictor 124, Equation (2) below. Doing so may adjust, based at least on the length change dL, the size of the hidden vector set $h=(h_1, h_2, \ldots, h_{|\tilde{L}|})$ such that the output of the length transformer 120 is a transformed hidden vector sequence $z=(z_1, \ldots, z_{|\tilde{L}|+dL})$ having an $\tilde{L}+dL$ quantity of transformed hidden vectors. As shown in FIG. 10A, the transformed hidden vector sequence z may be passed to the decoder 136 to generate the output sequence 140.

$$z_t = \sum_{t'=1}^{|\tilde{L}|} \omega_{t,t'}^t h_{t'} \qquad (2)$$

wherein $$\omega_{t,t'}^t \propto \exp\left(-\beta \left| \frac{t}{|\tilde{x}| + \Delta l} - \frac{t'}{|\tilde{x}|} \right|\right).$$

Figure 10B:
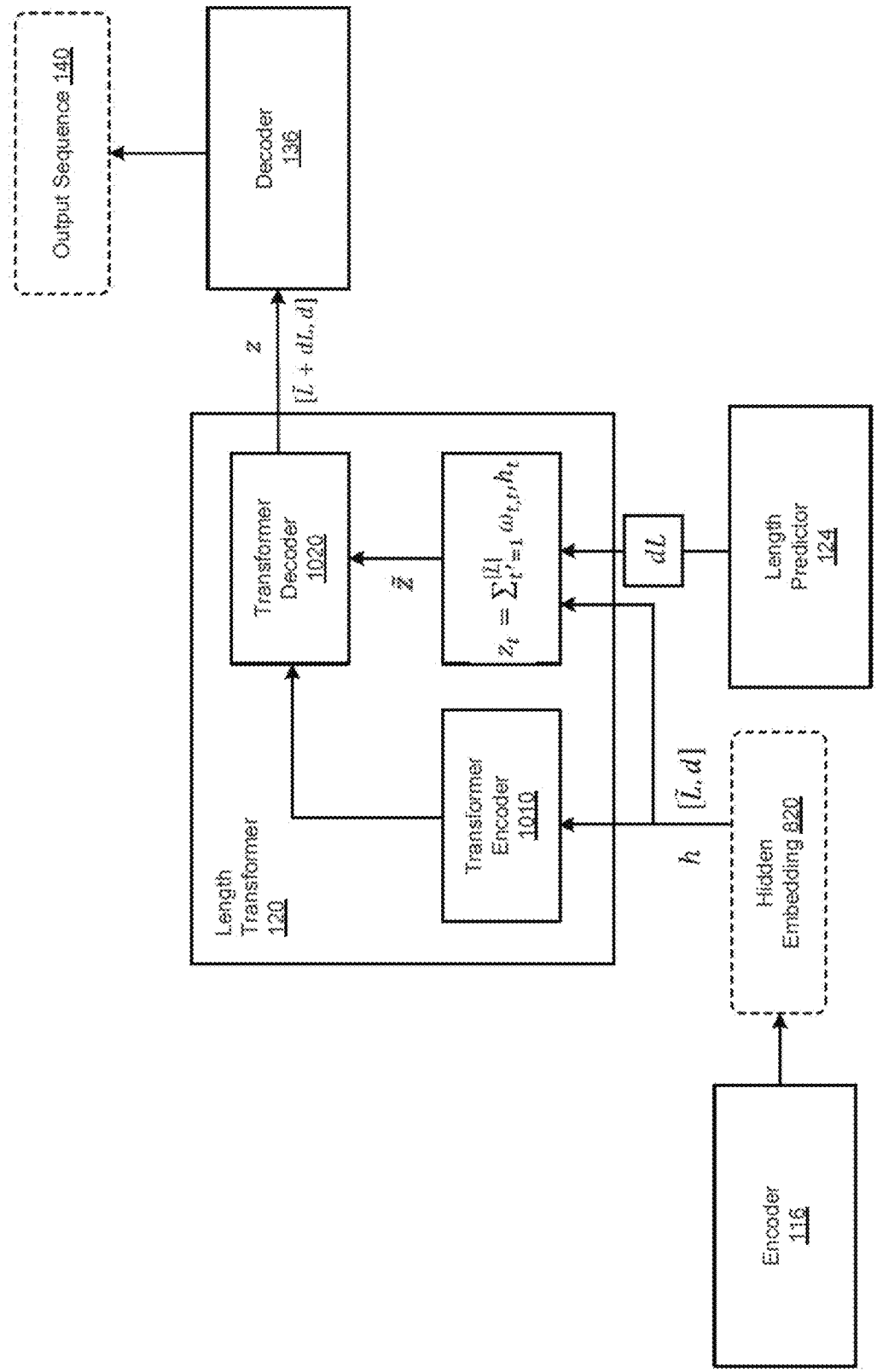
FIG. 10B depicts a block diagram illustrating another example of a length transformer, in accordance with some example embodiments.

FIG. 10B depicts a block diagram illustrating another example of the length transformer 120, in accordance with some example embodiments. Where the length transformer 120 merely applies Equation (2), as in the example shown in FIG. 10A, the length transformer 120 lacks a memory mechanism to recall the portions of the hidden embedding 820 it has already encountered and the length changes applied therein. Accordingly, where the length transformer 120 merely applies Equation (2), the distribution of length differences amongst the protein sequences output by the protein design computational model 115 do not sufficiently match that found amongst known protein sequences. As such, in some example embodiments, the length transformer 120 may be implemented using a transformer deep learning model which includes, as shown in FIG. 10B, a transformer encoder 1010 and a transformer decoder 1020. The transformer encoder 1010 may include an encoder stack of one or more successive encoding layers whereas the transformer decoder 1020 may include a decoder stack of one or more successive decoding layers. Implemented in this manner, a first length change that is applied to a portion of the hidden embedding 820 may be determined based on a second length change already applied to one or more preceding portions of the hidden embedding 820.

As shown in FIG. 10B, the transformer encoder 1010 may operate on an input that includes the hidden vector set $h=(h_1, h_2, \ldots, h_{|\tilde{L}|})$ of the hidden embedding 820. Meanwhile, the transformer decoder 1020 may operate on the output of the transformer encoder 1010 and an intermediary hidden vector sequence $\tilde{z}$ generated by applying Equation (2) to the hidden vector set $h=(h_1, h_2, \ldots, h_{|\tilde{L}|})$. Equation (2) may be applied based on the length change dL determined by the length predictor 124 such that the intermediary hidden vector sequence $\tilde{z}$ an $\tilde{L}+dL$ quantity of transformed hidden vectors. The transformer decoder 1020 may generate, based at least on the encodings of the hidden embedding 820 output by the transformer encoder 1010 and the intermediary hidden vector sequence $\tilde{z}$, the transformed hidden vector sequence z. FIG. 10B shows that the transformed hidden vector sequence z may be passed to the decoder 136 to generate the output sequence 140.

FIG. 2 depicts a chart 200 illustrating an example of a t-distributed stochastic neighbor embedding (t-SNE) of protein lyses generated by applying the protein design computational model 115, in accordance with some example embodiments. As shown in FIG. 2, the protein design computational model 115 is able to efficiently produce rich protein representations that could be used in many protein-related downstream tasks. By analysing low-dimensional embeddings of lyases (a class of enzymes that catalyze the breaking of various chemical bonds), the protein design computational model 115 is shown to be capable of identifying clusters of lyases that perform even more specific functions. A non-redundant set (with 90 percent sequence identity) of approximately 15000 protein lyases was retrieved from the Uniprot database.

FIG. 3 depicts a schematic diagram illustrating an example of a protein sequence redesigned by conditioning on an ion transmembrane transporter activity function, in accordance with some example embodiments. Referring to FIG. 3, the protein design computational model 115 may be applied to perform a process 300 in which an output protein sequence was generated by substantially altering an input protein sequence, in this case a Beta-2-microglobulin protein sequence (PDB: 4N0F, chain B) having primarily beta-sheets. The traversal of the topological space (e.g., manifold) learned by the protein design computational model 115 through training and the sampling of candidate protein sequences therefrom may commence at a starting position corresponding to the input protein sequence. In the example shown in FIG. 3, the output protein sequences identified by the protein design computational model 115 may exhibit novel secondary structures, such as an all alpha helix fold (e.g., a secondary structure that is almost exclusively alpha helical) starting from a sequence having all beta fold (e.g., a secondary structure that is almost exclusively made of beta sheets). Multiple sampling iterations (such as Marko Chain Monte Carlo (MCMC) sampling) may be performed by conditioning on the desired function ion transmembrane transporter activity (specified as GO:0015075 in the Gene Ontology database). In particular, the output protein sequence of alpha helical protein was obtained by altering the sequence of a beta protein by conditioning the sampling process with ion transmembrane transporter activity function label. Alpha helices are the most common protein structure elements embedded in membranes having this function, and so the designed sequence is expected to include alpha helices. The outputs of seven sampling iterations are shown in FIG. 3. The output protein sequence has no known homologs in the protein database (PDB), and exhibits maximally a 36% sequence identity to the protein sequences found in the Uniprot database. The output protein sequence generated by the protein design computational model 115 are therefore novel. Moreover, when the output protein sequence is folded to determine its tertiary structure (e.g., by the analysis engine 121 performing the structural modeling 125), the output protein sequence was determined to exhibit the desired function.

Figure 4:
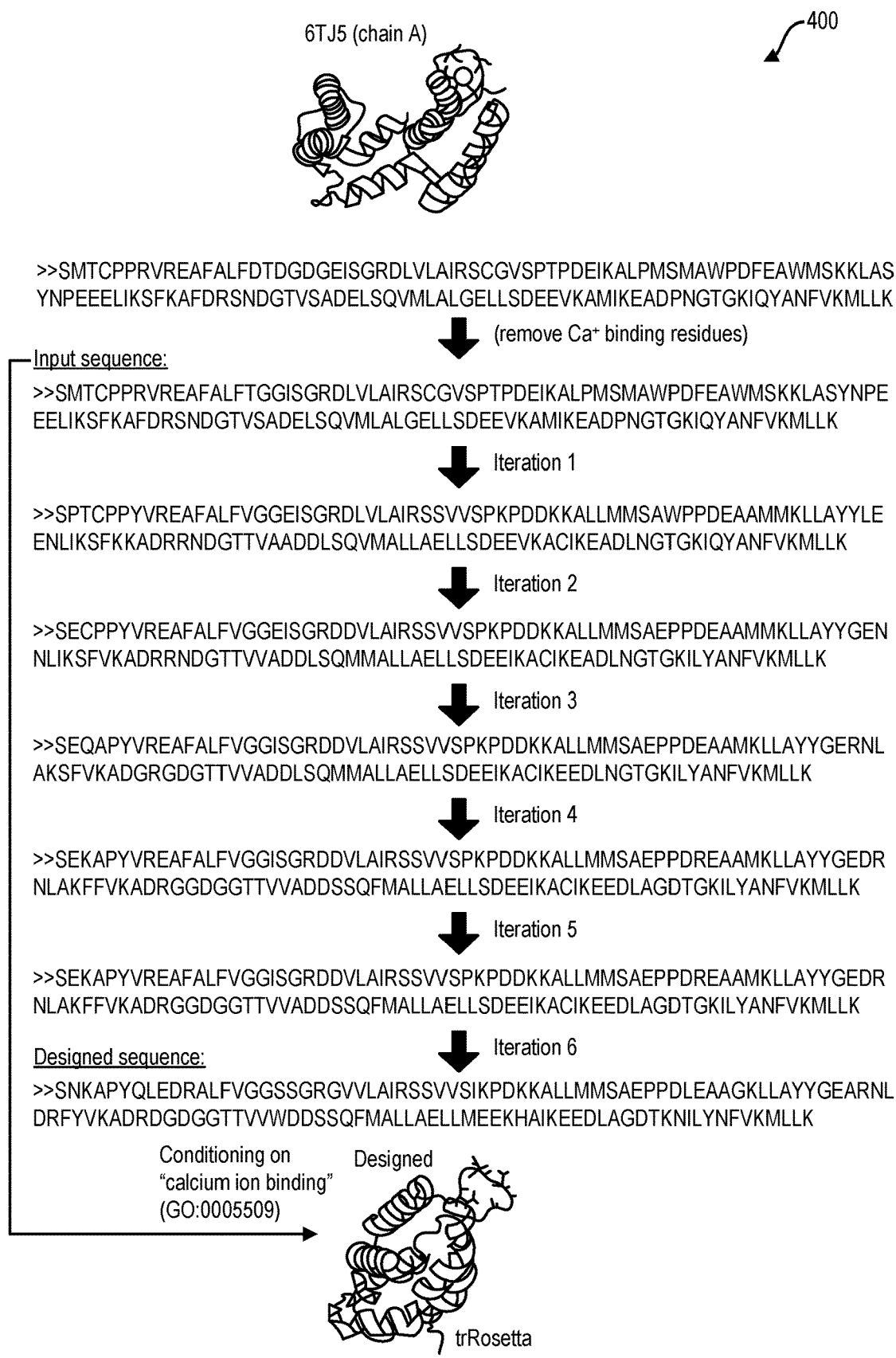
FIG. 4 depicts a schematic diagram illustrating an example of a protein sequence redesigned by conditioning on a metal binding function, in accordance with some example embodiments.
Figure 5A:
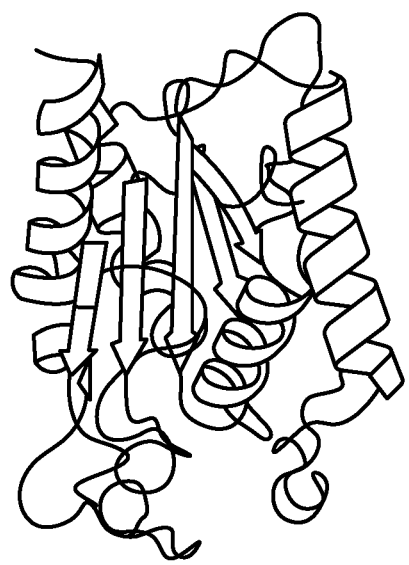
FIG. 5 depicts a schematic diagram illustrating an example of a process for redesigning the functions of cutinases, in accordance with some example embodiments.
Figure 5B:
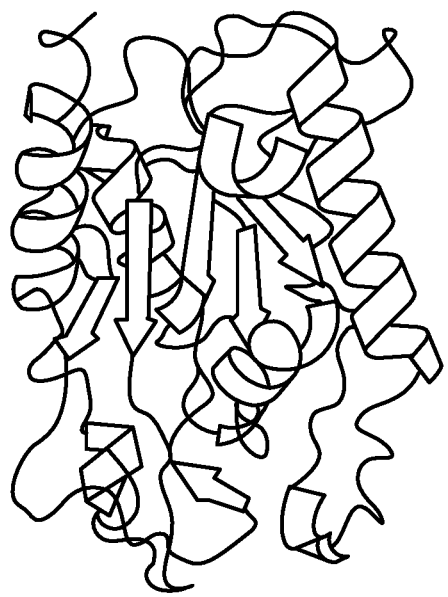
Figure 5C:
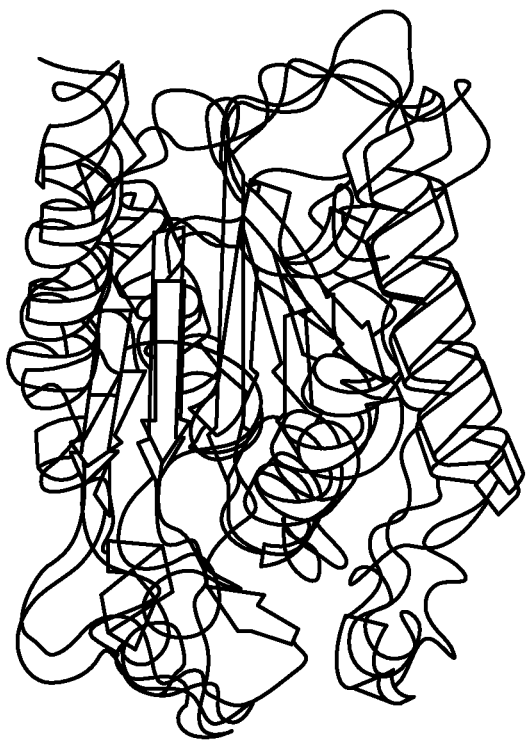
Figure 5D:
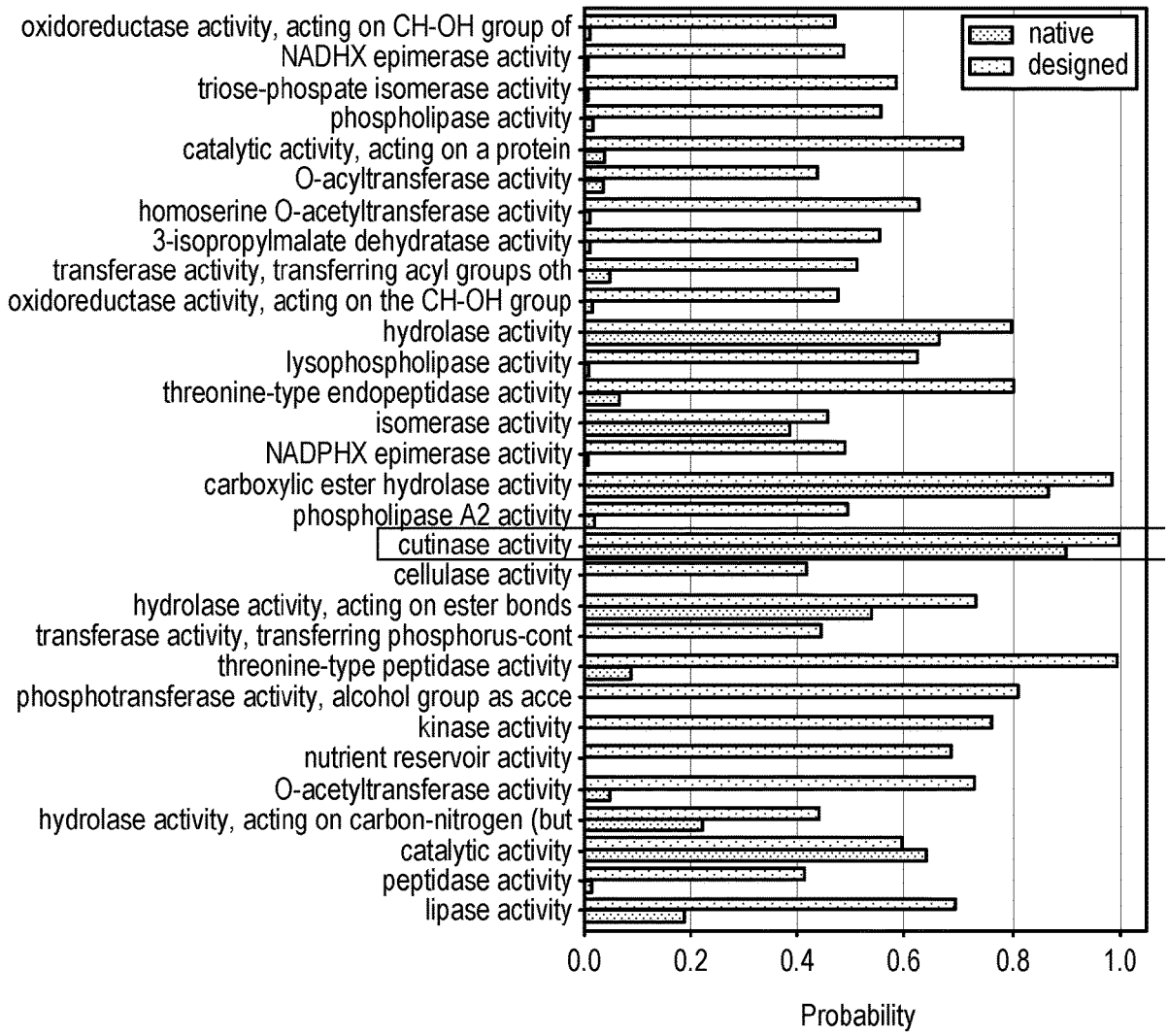

FIG. 4 depicts a schematic diagram illustrating an example of a protein sequence redesigned by conditioning on a metal binding function, in accordance with some example embodiments. As shown in FIG. 4, the protein design computational model 115 may be applied to perform a process 400 and generate a output protein sequence having one or more metal binding sites. The ability of the protein design computational model 115 to recover metal binding sites was tested by starting the sampling procedure from a protein sequence with its metal binding residue removed. In particular, a sequence of a calcium-binding protein (PDB: 6TJ5, chain A) with all amino acid residues involved in calcium binding (3 aspartate and 1 glutamic amino acid residues) removed is used as the input protein sequence provided to the protein design computational model 115. Starting from this input protein sequence, the sampling procedure (e.g., the Markov Chain Monte Carlo (MCMC) sampling) was performed by conditioning on calcium ion binding (GO:0005509). After six sampling iterations, a protein sequence exhibiting a calcium ion binding function was identified. This protein sequence exhibits a sequence motif present in a large proportion of known calcium binding proteins, including the original input protein sequence before the removal of the calcium ion binding sites. The output protein sequence has 48.7% sequence identity to the original input protein sequence. When folded, the output protein sequence forms a helix-loop-helix structural domain typical for this binding site in most calcium ion binding proteins. The residues in the loop (3 aspartate amino acids) are negatively charged and are therefore capable of interacting with positively charged calcium ion. Glycine is necessarily due to the conformational requirements of the backbone.

FIG. 5 depicts a schematic diagram illustrating an example of a process 500 for redesigning the functions of cutinases, in accordance with some example embodiments. FIG. 5(*a*) shows the native structure of *Fusarium solani pisi* cutinase (PDB ID: 1AGY, chain A), which is used as the input protein sequence to the protein design computational model 115. The output protein sequence generated by the protein design computational model 115, in this case after six sampling iterations while being conditioned on cutinase activity (GO:0050525), is shown in FIG. 5(*b*) with the catalytic residues in the protein sequence highlighted along with the predicted tertiary structure of the output protein sequence. At FIG. 5(*c*), a structural alignment between the original input protein sequence and the output protein sequence is shown. At FIG. 5(*d*), gene ontology term assignment probabilities of the input protein structure and the output protein structure scored by the function classifier 128 are shown. Multiple sequence alignment of top scoring sampled protein sequences showing the catalytic residues of the initial cutinase (1AGY-A) preserved by the manifold sampling strategy is depicted in FIG. 5(*e*).

Figure 6:
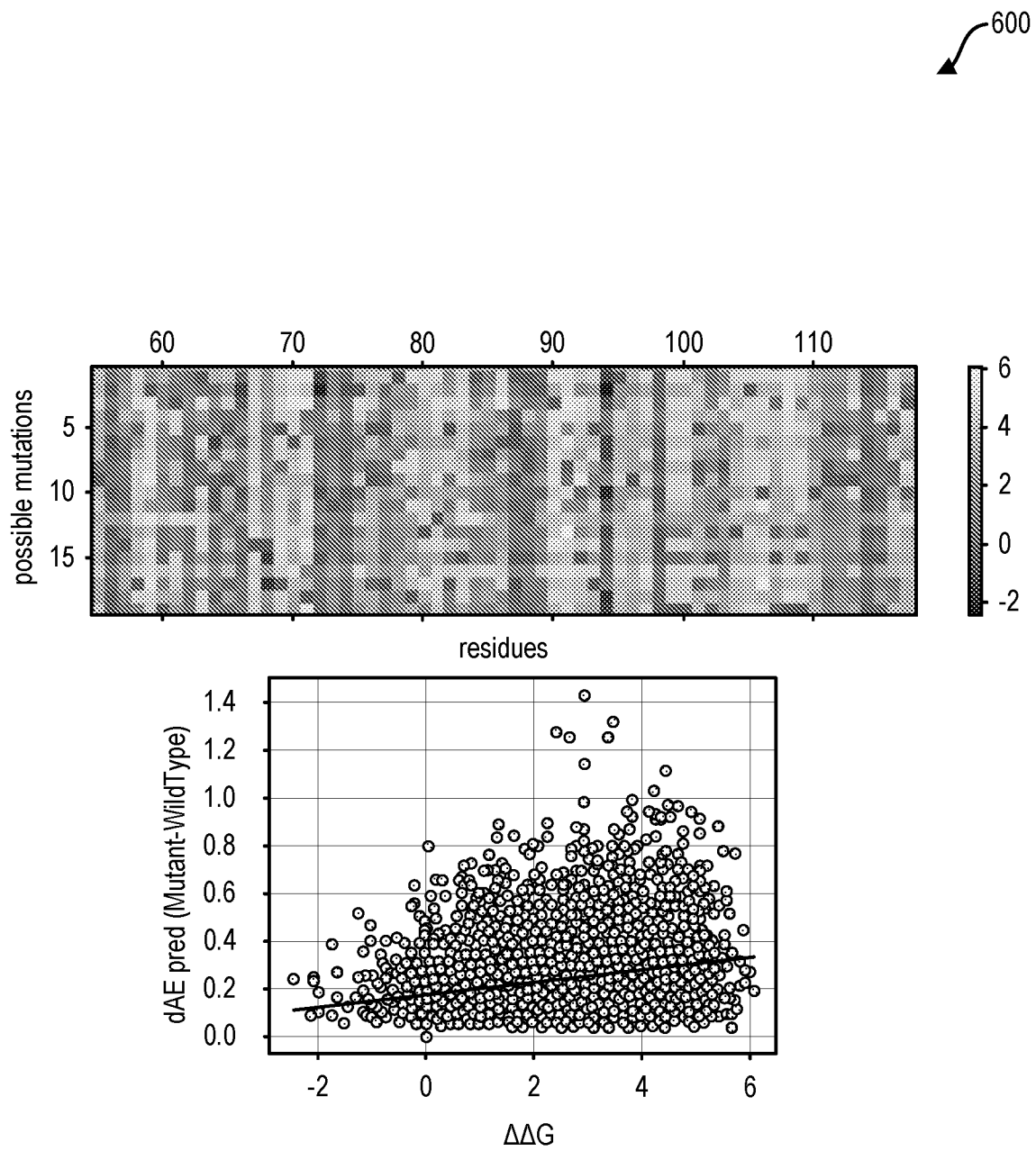
FIG. 6 depicts graphs illustrating the mutation-effect scores for $\beta$-lactamase, in accordance with some example embodiments.

FIG. 6 depicts graphs 600 illustrating the mutation-effect scores for β-lactamase, in accordance with some example embodiments. The graphs 600 correlate features of protein sequences generated using the protein design computational model 115 with experimental mutations. In particular, mutation-effect scores are depicted for positions 24-286 in the beta lactamase based on data from Uniprot: BLAT_ECOLX.

Figure 7:
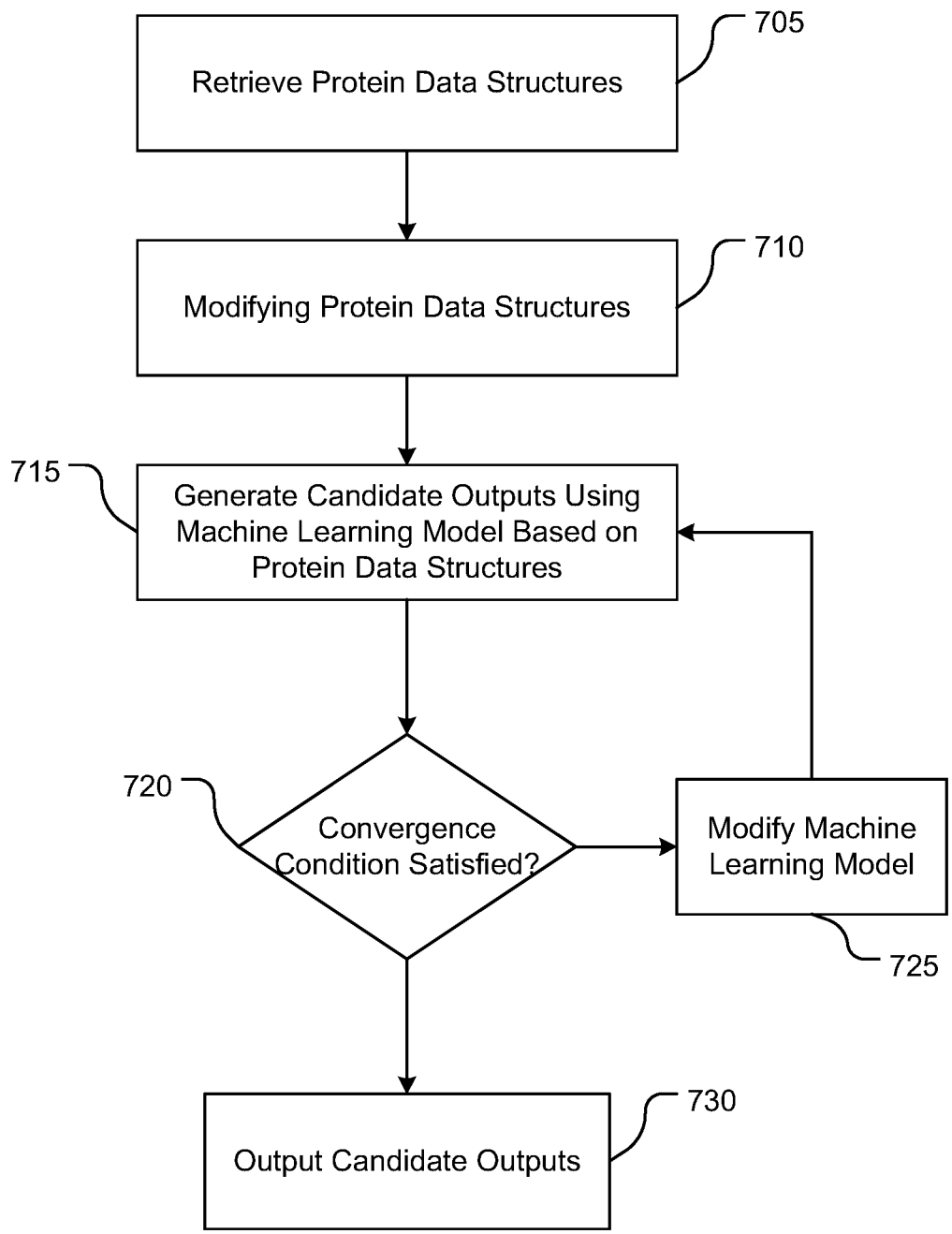
FIG. 7 depicts a flowchart illustrating an example of a process for training a function-guided protein design system, in accordance with some example embodiments.

FIG. 7 illustrates an example of a method 700 for training an in-silico function-guided protein design. The method 700 can be performed using various systems and modules described herein, including one or more components of the protein design system 100.

At 705, a plurality of protein data structures are retrieved. The protein data structures (sequences or groups of sequences) can be retrieved from a protein database, such as the Pfam database or several large sequence databases. The protein data structures can be data structures that include one or more elements identifying a respective amino acid of a sequence of amino acids (e.g., residues) corresponding to a particular protein.

At 710, the protein data structures are modified. Modifying the protein data structures can include adding, removing, or changing one or more residues (e.g., amino acids) of the protein data structures. For example, a particular residue of the protein data structure can be identified (e.g., randomly selected), and removed from the protein data structure, or modified by being replaced with a randomly selected amino acid. Adding a residue can include selecting (e.g., randomly selecting) a position along the protein data structure adjacent to one or more residues, and inserting an amino acid at the selected position.

At 715, a machine learning model can generate candidate outputs responsive to receiving the modified protein data structures. The candidate outputs can be protein data structures. The machine learning model can be a stacked MHA model.

At 720, a convergence condition can be evaluated based on the candidate outputs. The convergence condition can be a condition indicative of whether the machine learning model has reached a trained state. For example, the convergence condition can include at least one of a threshold number of iterations (e.g., iterations of generating the candidate outputs, modifying the machine learning model, and/or evaluating the convergence condition) or an optimization condition. For example, the optimization condition can be a score of a comparison of the candidate outputs to a target, such as by comparing a function of the candidate outputs with a function of the protein data structures (e.g., prior to modification).

At 725, responsive to the convergence condition not being satisfied, the machine learning model can be modified. For example, various characteristics of the machine learning model, such as one or more weights or biases associated with one or more layers of the machine learning model, can be modified. The machine learning model can be modified to reduce a difference between the candidate output and the plurality of protein data structures, such as to reduce a difference between functions identified for the candidate output and functions identified for the plurality of protein data structures. For example, at least one function assignment assigned to at least a subset of the plurality of protein data structures can be retrieved (e.g., using a function classifier or from a function database), and the machine learning model can be modified based on the at least one function assignment and a candidate function assignment of each modified protein data structure of the plurality of modified protein data structure corresponding to the subset. The function classifier can be trained as a machine learning model (e.g., second machine learning model), including by simultaneously operating on the modified protein data structures to generate candidate outputs which can be evaluated relative to the function assignments of the protein data structures.

At 730, responsive to the convergence condition being satisfied, the candidate outputs can be outputted. For example, the candidate outputs can be outputted to be evaluated for validating or confirming the training of the machine learning models, such as to validate the ability of the machine learning models to recover functions of the original protein data structures.

Figure 11:
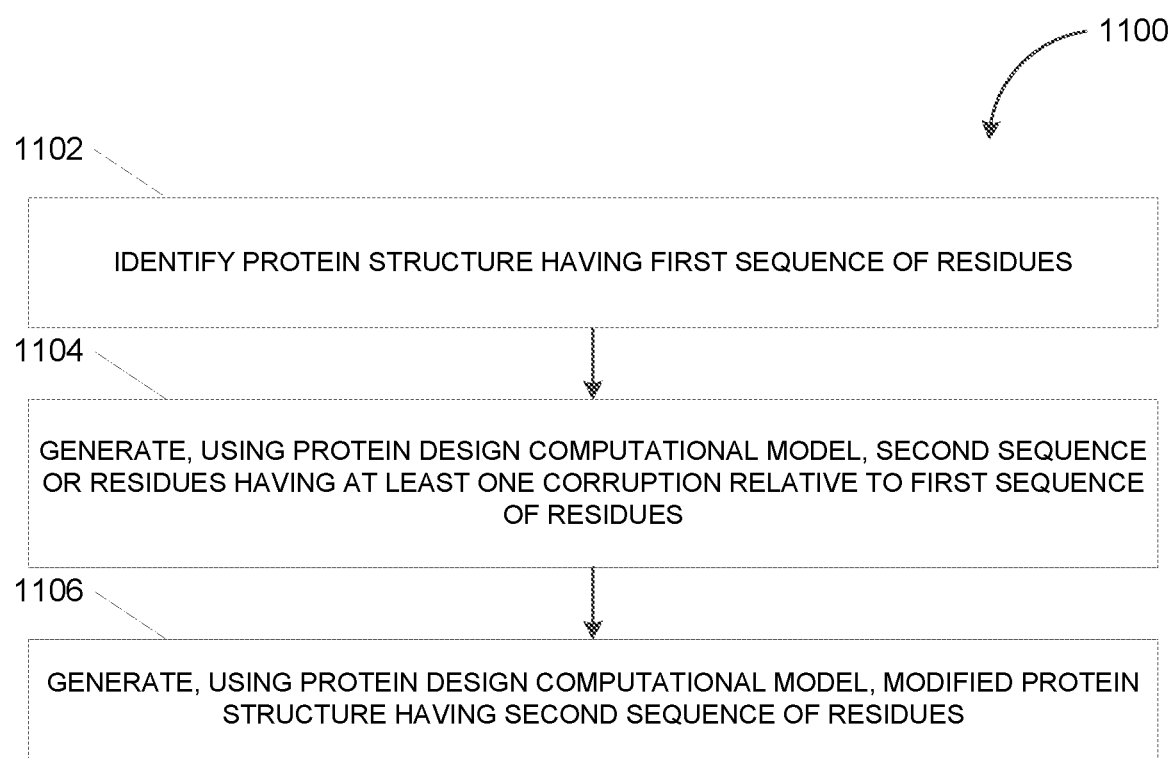
FIG. 11 depicts a flowchart illustrating an example of a process for function guided in silico protein design, in accordance with some example embodiments.

FIG. 11 depicts a flowchart illustrating an example of a process 1100 for function guided in silico protein design, in accordance with some example embodiments. Referring to FIGS. 1-11, the process 1100 may be performed by the protein design engine 110 to generate one or more protein sequences. For example, in some example embodiments, the protein design engine 110 may apply the protein design computational model 115 to generate, based at least on a first protein sequence with or without a desired function, a second protein sequence having the desired function.

At 1102, the protein design engine 110 may identify a protein structure having a first sequence of residues. For example, as shown in FIG. 1B, the protein design engine 110 may retrieve the input sequence 108 from the protein database 104, which maintains a variety of protein data structures representative of proteins. Alternatively and/or additionally, the protein design engine 110 may receive, from the client device 130, one or more user inputs identifying the input sequence 108. In some example embodiments, the input sequence 108 may be a protein sequence X having a length of L corresponding to an L quantity of amino acid residues. In some instances, the input sequence 108 may exhibit a desired function, in which case the protein design engine 110 may modify the input sequence 108 to generate the output sequence 140 such that the output sequence 140 is a different protein sequence that also exhibits the desired function. Alternatively and/or additionally, the input sequence 108 may lack the desired function and/or exhibit an undesired function, in which case the protein design engine 110 may modify the input sequence 108 to generate the output sequence 140 such that the output sequence 140 is a different protein sequence that exhibits the desired function but not the undesired function.

At 1104, the protein design engine 110 may use a protein design computational model to generate a second sequence of residues having at least one corruption relative to the first sequence of residues. In some example embodiments, the protein design engine 110 may generate the output sequence 140 by applying the protein design computational model 115, which may be implemented as one or more machine learning models (e.g., autoencoders and/or the like). For example, the protein design computational model 115 may be applied to sample a data distribution (e.g., a topological space such as a manifold occupied by the known protein sequences) learned by the protein design computational model 115 through training. The data distribution may correspond to a reduced dimensional representation of the sequences of residues forming a variety of known protein sequences. Accordingly, by sampling from the data distribution, such as by traversing the topological space (e.g., manifold) with the input sequence 108 as the starting point, the protein design engine 110 may identify candidate protein sequences with a high probability of exhibiting the desired function, especially when compared to an indiscriminate exploration of the combinatorial search space of every possible permutation of amino acid residues that can form a protein structure.

In some example embodiments, the sampling of the data distribution includes the protein design computational model 115 generating an encoding of the input sequence 108 before decoding an intermediate sequence, such as the length transformed hidden embedding 830, which exhibits at least one of a corruption (e.g., an insertion, a deletion, and/or a modification of an amino acid residue) or a length change relative to the input sequence 108. The protein design engine 110 may perform multiple sampling iterations, with each sampling iteration identifying at least one candidate protein sequence. Examples of techniques to iteratively sample from the data distribution includes a Markov Chain Monte Carlo (MCMC), importance sampling (IS), rejection sampling, Metropolis-Hastings, Gibbs sampling, slice sampling, exact sampling, and/or the like.

Candidate protein sequences may be subjected to further functional and/or structural analysis to determine, for example, whether each candidate protein sequence exhibits a desired function. This functional and/or structural analysis may be performed on a latent space representation of a candidate protein sequence (e.g., prior to decoding by the decoder 136) or on a protein sequence space representation of the candidate protein sequence (e.g., subsequent to decoding by the decoder 136). For example, as shown in FIG. 1B, the protein design computational model 115 may include an embedded function classifier 128 trained to determine, based at least on the intermediary representation of each candidate protein sequence (e.g., the length transformed hidden embedding 830), one or more functions of the protein sequence. Alternatively and/or additionally, FIG. 1A shows that the candidate protein sequences may be evaluated by the analysis engine 121, which may perform one or more of function prediction 123 (e.g., to determine one or more functions of the protein sequence), structural modeling 125 (e.g., to determine a secondary structure and/or a tertiary structure of the protein sequence), and molecular dynamics simulations 127 (e.g., to determine an energy state and stability of the protein sequence). It should be appreciated that a function guided sampling of the data distribution may significantly improve the computational efficiency associated with de novo protein design while maximizing the diversity and functionality of the resulting protein sequences.

At 1106, the protein design engine 110 may use the protein design computational model to generate a modified protein structure having the second sequence of residues. In some example embodiments, a modified protein structure corresponding to the output sequence 140 may be generated in silico upon satisfaction of one or more conditions. For example, in some cases, the protein design engine 110 may continue to sample the data distribution until one or more conditions are satisfied including, for example, the completion of a threshold quantity of sampling iterations, the identification of a threshold quantity of candidate protein sequences, the identification of a threshold quantity of protein sequences exhibiting a desired function and/or lacking an undesired function, and/or the like. In cases where a candidate protein sequence, such as the output sequence 140, is determined to exhibit certain desired functions, such as a binding affinity towards certain antigens, the protein design engine 110 may identify the output sequence 140 as a modified protein structure that is suitable for further in vitro analysis.

Figure 12:
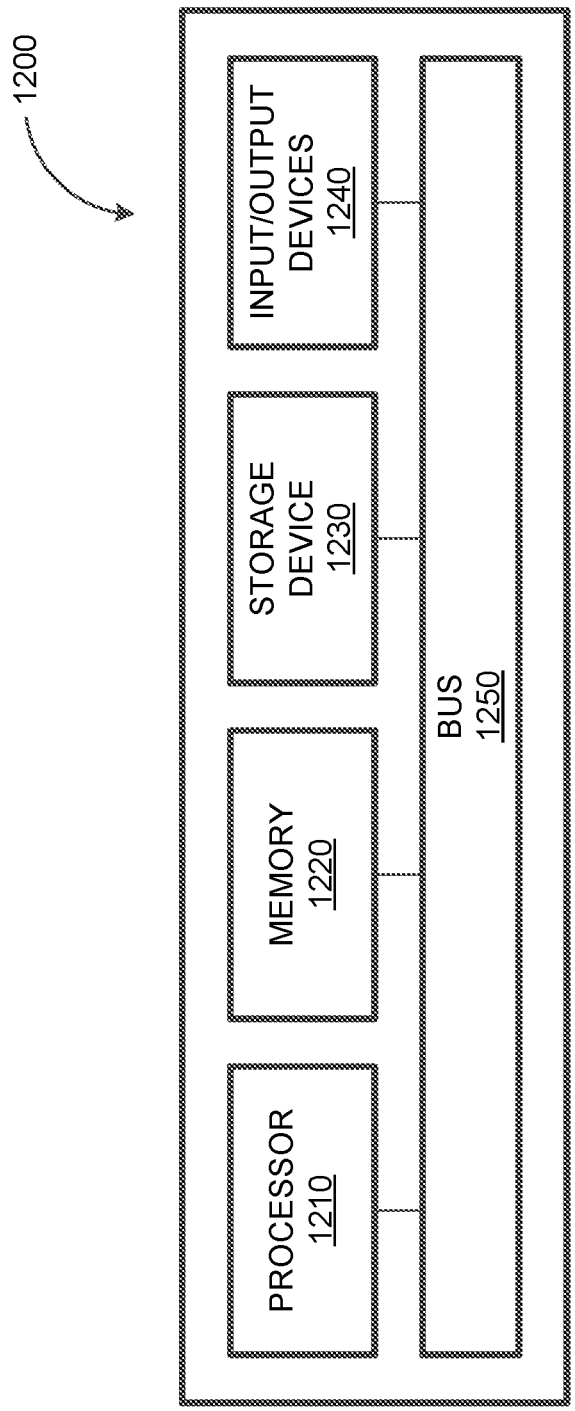
FIG. 12 depicts a block diagram illustrating an example of a computing system, in accordance with some example embodiments.

FIG. 12 depicts a block diagram illustrating an example of computing system 1200, in accordance with some example embodiments. Referring to FIGS. 1-12, the computing system 1200 may be used to implement the protein design engine 110, the analysis engine 121, the client device 130 and/or any components therein.

As shown in FIG. 12, the computing system 1200 can include a processor 1210, a memory 1220, a storage device 1230, and an input/output device 1240. The processor 1210, the memory 1220, the storage device 1230, and the input/output device 1240 can be interconnected via a system bus 1250. The processor 1210 is capable of processing instructions for execution within the computing system 1200. Such executed instructions can implement one or more components of, for example, the protein design engine 110, the analysis engine 121, the client device 130, and/or the like. In some example embodiments, the processor 1210 can be a single-threaded processor. Alternately, the processor 1210 can be a multi-threaded processor. The processor 1210 is capable of processing instructions stored in the memory 1220 and/or on the storage device 1230 to display graphical information for a user interface provided via the input/output device 1240.

The memory 1220 is a computer readable medium such as volatile or non-volatile that stores information within the computing system 1200. The memory 1220 can store data structures representing configuration object databases, for example. The storage device 1230 is capable of providing persistent storage for the computing system 1200. The storage device 1230 can be a floppy disk device, a hard disk device, an optical disk device, or a tape device, or other suitable persistent storage means. The input/output device 1240 provides input/output operations for the computing system 1200. In some example embodiments, the input/output device 1240 includes a keyboard and/or pointing device. In various implementations, the input/output device 1240 includes a display unit for displaying graphical user interfaces.

According to some example embodiments, the input/output device 1240 can provide input/output operations for a network device. For example, the input/output device 1240 can include Ethernet ports or other networking ports to communicate with one or more wired and/or wireless networks (e.g., a local area network (LAN), a wide area network (WAN), the Internet).

In some example embodiments, the computing system 1200 can be used to execute various interactive computer software applications that can be used for organization, analysis and/or storage of data in various formats. Alternatively, the computing system 1200 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1240. The user interface can be generated and presented to a user by the computing system 1200 (e.g., on a computer screen monitor, etc.).

Embodiments of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The operations described in this specification can be performed by a data processing apparatus on data stored on one or more computer-readable storage devices or received from other sources. The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, subprograms, or portions of code). A computer program can be deployed to be executed on one computer or on multiple computers that are located at one site or distributed across multiple sites and interconnected by a communication network.

Processors suitable for the execution of a computer program include, by way of example, microprocessors, and any one or more processors of a digital computer. A processor can receive instructions and data from a read only memory or a random access memory or both. The elements of a computer are a processor for performing actions in accordance with instructions and one or more memory devices for storing instructions and data. A computer can include, or be operatively coupled to receive data from or transfer data to, or both, one or more mass storage devices for storing data, e.g., magnetic, magneto optical disks, or optical disks. A computer need not have such devices. Moreover, a computer can be embedded in another device, e.g., a personal digital assistant (PDA), a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The implementations described herein can be implemented in any of numerous ways including, for example, using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to or receive communications from other devices. The display unit(s) may be provided, for example, to allow a user to view various information in connection with execution of the instructions. The user input device(s) may be provided, for example, to allow the user to make manual adjustments, make selections, enter data or various other information, or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the solution discussed above. The computer readable medium or media can be transportable, such that the program or programs stored thereon can be loaded onto one or more different computers or other processors to implement various aspects of the present solution as discussed above.

The terms "program" or "software" are used herein to refer to any type of computer code or set of computer-executable instructions that can be employed to program a computer or other processor to implement various aspects of embodiments as discussed above. One or more computer programs that when executed perform methods of the present solution need not reside on a single computer or processor, but may be distributed in a modular fashion amongst a number of different computers or processors to implement various aspects of the present solution.

Computer-executable instructions may be in many forms, such as program modules, executed by one or more computers or other devices. Program modules can include routines, programs, objects, components, data structures, or other components that perform particular tasks or implement particular abstract data types. The functionality of the program modules can be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A protein design system, comprising:
   an autoencoder coupled with a length prediction machine learning model, a length transformation machine learning model, and a function classification machine learning model, where the protein design system includes one or more processors; and
   at least one memory storing instructions, which when executed by the one or more processors, result in operations comprising:
      modifying an input sequence corresponding to a protein, the input sequence comprising a data structure indicating a plurality of amino acid residues of the protein;
      generating, by an encoder comprising the coupled autoencoder, a latent space sequence representation of the modified sequence,
         where the encoder has been trained to generate the latent space sequence representation to occupy a position in a latent space indicative of a relationship between the modified sequence and one or more populations of protein sequences exhibiting structural similarities and/or functional similarities;
      predicting, by the length prediction machine learning model, a length difference between the latent space sequence representation and a target sequence corresponding to a different protein based on at least one target function of the target sequence;
      applying, by the length transformation machine learning model, the length difference to the latent space sequence representation to generate a length transformed latent space sequence representation; and
      identifying, by the function classification machine learning model, at least one sequence function of the length transformed latent space sequence representation;
      upon determining that the at least one sequence function of the length transformed latent space sequence representation satisfies one or more thresholds, generating, by a decoder, the target sequence where the decoder comprises the coupled autoencoder, where the decoder has been trained to generate the target sequence by determining, based at least on the length transformed latent space sequence representation, an identity of each amino acid residue in the target sequence, and where the decoder generates the target sequence by at least generating a data structure indicating a plurality of amino acid residues comprising the target sequence.

2. The protein design system of claim 1, wherein the input sequence is modified by at least one of modifying an identity of an amino acid residue in the input sequence, removing an amino acid residue from the input sequence, or inserting an amino acid residue into the input sequence.

3. The protein design system of claim 1, wherein the operations further comprise:
upon determining that the at least one sequence function of the length transformed latent space sequence representation fails to satisfy the one or more thresholds, modifying the input sequence to generate another modified sequence.

4. The protein design system of claim 3, wherein the at least one target function comprises a plurality of target functions.

5. The protein design system of claim 1, wherein at least one of the encoder, the length prediction machine learning model, the function classification machine learning model, the length transformation machine learning model, or the decoder comprises a multi-head attention machine learning model.

6. The protein design system of claim 1, wherein the input sequence includes at least one of (i) a randomly selected residue, (ii) a predetermined difference from the target sequence, or (iii) a function classification score for the at least one target function that fails to satisfy the one or more thresholds.

7. The protein design system of claim 1, wherein the operations further comprise:
generating at least one of a secondary structure score or a conformational energy score for the target sequence.

8. A computer implemented method, comprising:
generating a target sequence using a protein design system, the protein design system including an autoencoder coupled with a length prediction machine learning model, a length transformation machine learning model, and a function classification machine learning model, and the protein design system generating the target sequence by at least:
modifying an input sequence corresponding to a protein, the input sequence comprising a data structure indicating a plurality of amino acid residues of the protein;
generating, by an encoder comprising the coupled autoencoder, a latent space sequence representation of the modified sequence,
where the encoder has been trained to generate the latent space sequence representation to occupy a position in a latent space indicative of a relationship between the modified sequence and one or more populations of protein sequences exhibiting structural similarities and/or functional similarities;
predicting, by the length prediction machine learning model, a length difference between the latent space sequence representation and the target sequence corresponding to a different protein based on at least one target function of the target sequence;
applying, by the length transformation machine learning model, the length difference to the latent space sequence representation to generate a length transformed latent space sequence representation; and
identifying, by the function classification machine learning model, at least one sequence function of the length transformed latent space sequence representation;
upon determining that the at least one sequence function of the length transformed latent space sequence representation satisfies one or more thresholds, generating, by a decoder, the target sequence,
where the decoder comprises the coupled autoencoder,
where the decoder has been trained to generate the target sequence by determining, based at least on the length transformed latent space sequence representation, an identity of each amino acid residue in the target sequence, and
where the decoder generates the target sequence by at least generating a data structure indicating a plurality of amino acid residues comprising the target sequence.

9. The method of claim 8, wherein the input sequence is modified by at least one of modifying an identity of an amino acid residue in the input sequence, removing an amino acid residue from the input sequence, or inserting an amino acid residue into the input sequence.

10. The method of claim 8, further comprising:
upon determining that the at least one sequence function of the length transformed latent space sequence representation fails to satisfy the one or more thresholds, modifying the input sequence to generate another modified sequence.

11. The method of claim 10, wherein the at least one target function comprises a plurality of target functions.

12. The method of claim 8, wherein at least one of the encoder, the length prediction machine learning model, the function classification machine learning model, the length transformation machine learning model, or the decoder comprises a multi-head attention machine learning model.

13. The method of claim 8, wherein the input sequence includes at least one of (i) a randomly selected residue, (ii) a predetermined difference from the target sequence, or (iii) a function classification score for the at least one target function that fails to satisfy the one or more thresholds.

14. The method of claim 8, further comprising:
generating at least one of a secondary structure score or a conformational energy score for the target sequence.

15. A non-transitory computer readable medium storing instructions, which when executed by one or more processors, result in operations comprising:
generating a target sequence using a protein design system, the protein design system including an autoencoder coupled with a length prediction machine learning model, a length transformation machine learning model, and a function classification machine learning model, and the protein design system generating the target sequence by at least:
modifying an input sequence corresponding to a protein, the input sequence comprising a data structure indicating a plurality of amino acid residues of the protein;

generating, by an encoder comprising the coupled autoencoder, a latent space sequence representation of the modified sequence, where the encoder has been trained to generate the latent space sequence representation to occupy a position in a latent space indicative of a relationship between the modified sequence and one or more populations of protein sequences exhibiting structural similarities and/or functional similarities;

predicting, by the length prediction machine learning model, a length difference between the latent space sequence representation and the target sequence corresponding to a different protein based on at least one target function of the target sequence;

applying, by the length transformation machine learning model, the length difference to the latent space sequence representation to generate a length transformed latent space sequence representation; and identifying, by the function classification machine learning model, at least one sequence function of the length transformed latent space sequence representation;

upon determining that the at least one sequence function of the length transformed latent space sequence representation satisfies one or more thresholds, generating, by a decoder, the target sequence, where the decoder comprises the coupled autoencoder, where the decoder has been trained to generate the target sequence by determining, based at least on the length transformed latent space sequence representation, an identity of each amino acid residue in the target sequence, and where the decoder generates the target sequence by at least generating a data structure indicating a plurality of amino acid residues comprising the target sequence.

16. The method of claim 8, wherein the input sequence is modified by at least one of modifying an identity of an amino acid residue in the input sequence, removing an amino acid residue from the input sequence, or inserting an amino acid residue into the input sequence.

17. The method of claim 8, further comprising:
upon determining that the at least one sequence function of the length transformed latent space sequence representation fails to satisfy the one or more thresholds, modifying the input sequence to generate another modified sequence.

18. The method of claim 10, wherein the at least one target function comprises a plurality of target functions.

19. The method of claim 8, wherein at least one of the encoder, the length prediction machine learning model, the function classification machine learning model, the length transformation machine learning model, or the decoder comprises a multi-head attention machine learning model.

20. The method of claim 8, wherein the input sequence includes at least one of (i) a randomly selected residue, (ii) a predetermined difference from the target sequence, or (iii) a function classification score for the at least one target function that fails to satisfy the one or more thresholds.

21. The method of claim 8, further comprising:
generating at least one of a secondary structure score or a conformational energy score for the target sequence.

* * * * *